(12) United States Patent
Nitzan

(10) Patent No.: US 11,154,208 B2
(45) Date of Patent: Oct. 26, 2021

(54) SYSTEM AND METHOD OF MEASUREMENT OF AVERAGE BLOOD PRESSURE

(71) Applicant: JERUSALEM COLLEGE OF TECHNOLOGY, Jerusalem (IL)

(72) Inventor: Meir Nitzan, Beth El (IL)

(73) Assignee: JERUSALEM COLLEGE OF TECHNOLOGY, Jerusalem (IL)

( * ) Notice: Subject to any disclaimer, the term of this patent is extended or adjusted under 35 U.S.C. 154(b) by 623 days.

(21) Appl. No.: 15/775,898

(22) PCT Filed: Nov. 15, 2016

(86) PCT No.: PCT/IL2016/051228
§ 371 (c)(1),
(2) Date: May 14, 2018

(87) PCT Pub. No.: WO2017/085716
PCT Pub. Date: May 26, 2017

(65) Prior Publication Data
US 2018/0325398 A1 Nov. 15, 2018

Related U.S. Application Data

(60) Provisional application No. 62/255,564, filed on Nov. 16, 2015.

(51) Int. Cl.
*A61B 5/0225* (2006.01)
*A61B 5/021* (2006.01)
(Continued)

(52) U.S. Cl.
CPC ........ *A61B 5/02255* (2013.01); *A61B 5/0225* (2013.01); *A61B 5/02108* (2013.01);
(Continued)

(58) Field of Classification Search
None
See application file for complete search history.

(56) References Cited

U.S. PATENT DOCUMENTS 5,533,511 A 7/1996 Kaspari et al.
6,402,696 B1 6/2002 Nitzan et al.
(Continued)

FOREIGN PATENT DOCUMENTS

WO 99/39634 A1 8/1999

OTHER PUBLICATIONS

G. Drzewiecki, "Noninvasive assessment of arterial blood pressure and mechanics" In: Medical Instruments and Devices, CRC Press, 1995: 1196-1211.
(Continued)

*Primary Examiner* — Kaylee R Wilson
*Assistant Examiner* — Jay B Shah
(74) *Attorney, Agent, or Firm* — Browdy and Neimark, P.L.L.C.

(57) ABSTRACT

Techniques for determining average value of an arterial blood pressure parameter of an examined subject are disclosed. A pressure device is used to apply changing pressure conditions over a body part of a subject and generate pressure measurement data indicative of the pressure applied. A first measuring unit measures blood-pressure-pulse related signals in the pressure-affected body part, and generate blood-pressure-pulse related measurement data indicative thereof, and a second measuring unit measures blood-pressure-pulse related signals in a pressure-free body part of the examined subject, and generate reference blood-pressure-pulse related measurement data indicative thereof. A control unit is used to operate the pressure device to apply the changing pressure conditions over the pressure-affected body part and simultaneously operate the first and second (Continued)

measuring units, determine an initial blood pressure parameter value of the subject based on the measurement data from the pressure device and from the first measuring unit, determine a correction factor based on the measurement data from the second measuring unit and from the first measuring unit, and determine the average blood pressure parameter of the examined subject based on the initial blood pressure parameter value and the correction factor.

20 Claims, 9 Drawing Sheets

(51) Int. Cl.
*A61B 5/022* (2006.01)
*A61B 5/00* (2006.01)

(52) U.S. Cl.
CPC ...... *A61B 5/02116* (2013.01); *A61B 5/02125* (2013.01); *A61B 5/02208* (2013.01); *A61B 5/02225* (2013.01); *A61B 5/02233* (2013.01); *A61B 5/02241* (2013.01); *A61B 5/6826* (2013.01); *A61B 5/7203* (2013.01); *A61B 5/7278* (2013.01); *A61B 5/7282* (2013.01); *A61B 5/7221* (2013.01); *A61B 2562/0204* (2013.01); *A61B 2562/0233* (2013.01); *A61B 2562/0247* (2013.01); *A61B 2562/04* (2013.01)

(56) References Cited

U.S. PATENT DOCUMENTS

| 6,475,153 | B1 | 11/2002 | Mohammad et al. |
| 7,544,168 | B2 | 6/2009 | Nitzan |
| 2002/0095092 | A1 | 7/2002 | Kondo et al. |
| 2005/0192500 | A1 | 9/2005 | Caro et al. |
| 2006/0074322 | A1 | 4/2006 | Nitzan |
| 2007/0055163 | A1 | 3/2007 | Asada et al. |
| 2009/0099465 | A1 | 4/2009 | Jones et al. |
| 2010/0160798 | A1 | 6/2010 | Banet et al. |
| 2011/0066043 | A1 | 3/2011 | Banet et al. |
| 2014/0142434 | A1 | 5/2014 | Nitzan |

OTHER PUBLICATIONS

K.G. Ng and C.F. Small, "Survey of automated noninvasive blood pressure monitors", J. Clin. Eng. 19:452-475 (1994).

Nitzan et al. "Automatic noninvasive measurement of systolic blood pressure using photoplethysmography". BioMedical Engineering OnLine, 8:28 (2009).

Nitzan et al., "Effects of external pressure on arteries distal to the cuff during sphygmomanometry" IEEE Tr. BME. 52:1120-1127 (2005).

Nitzan et al,"The very low frequency variability in the arterial blood pressure and in the blood volume pulse.", Medical and Biological Engineering and Computing vol. 37, pp. 54-58 (1999).

International Search Report of PCT/IL2016/051228 dated Nov. 16, 2015.

OSCILLOMETRY

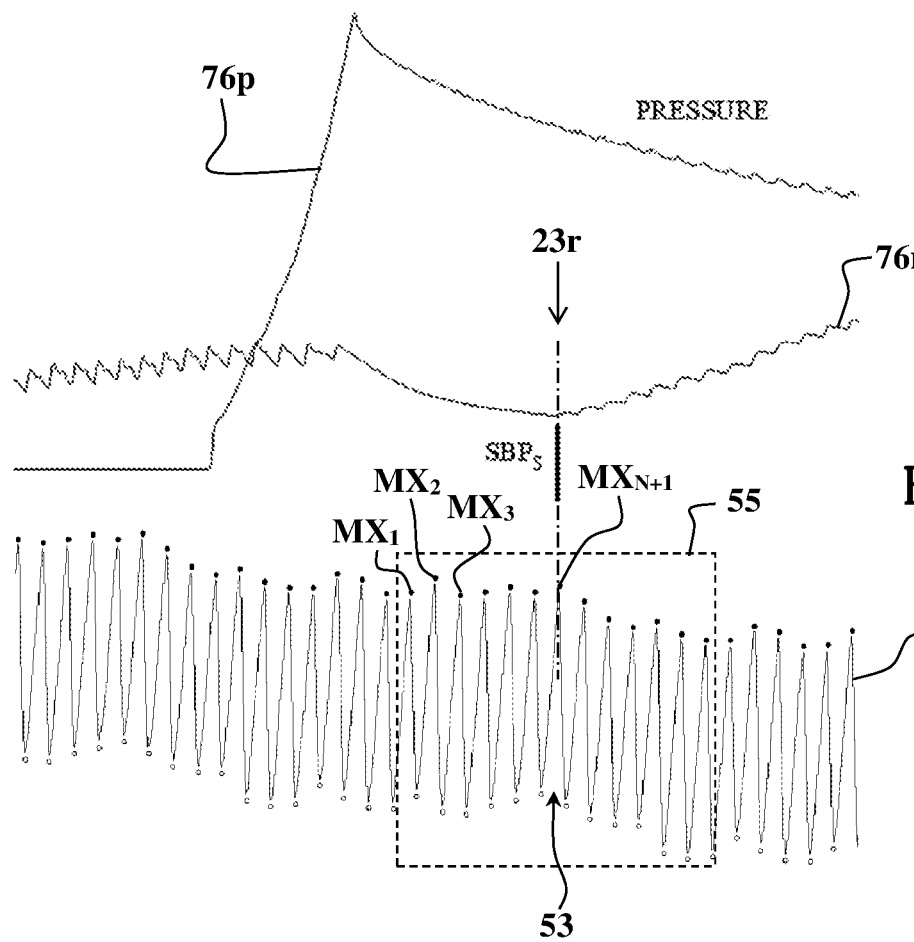
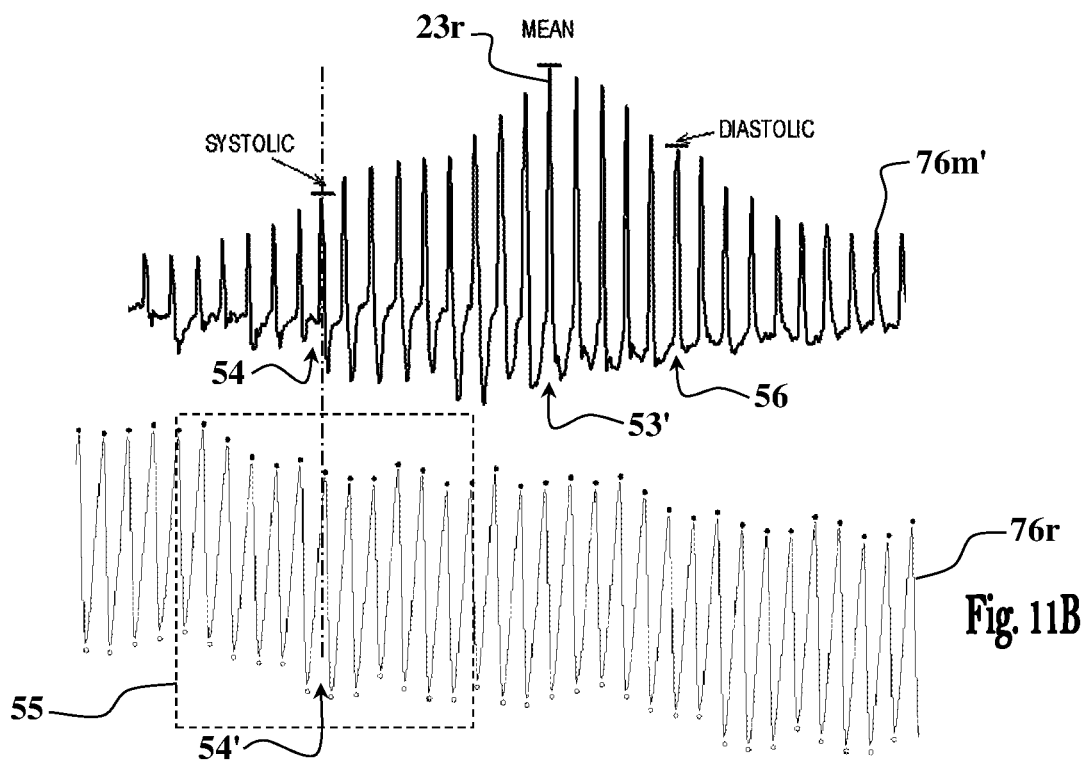

SYSTEM AND METHOD OF MEASUREMENT OF AVERAGE BLOOD PRESSURE

TECHNOLOGICAL FIELD

The present invention relates to evaluation of blood pressure of a subject by optical and pressure measurements.

BACKGROUND

The assessment of arterial blood pressure has both physiological and clinical significance, and tremendous efforts have been made to develop reliable noninvasive methods for measurement thereof. One common method for measuring blood pressure is manual Korotkoff-based sphygmomanometry, which is considered to be the most accurate noninvasive method, and to which other methods are usually compared. In manual Korotkoff-based sphygmomanometry an external inflatable cuff is utilized to apply a pressure greater than the systolic blood pressure over a limb followed by audible/acoustic detection of Korotkoff sounds by a stethoscope while the cuff pressure over the limb is gradually decreased (see, e.g., FIG. 1A).

However, manual Korotkoff-based sphygmomanometry is prone to several sources of errors, such as, for example, insufficient hearing acuity of the user and behavioral factors, which influence the level of blood pressure, such as the presence of a physician (also known as white coat hypertension). Some of these errors may be avoided when automatic measurement of the blood pressure is performed, and several methods have been suggested for automatic noninvasive blood pressure (NIBP) measurement. The most widely used of these automatic NIBP methods are oscillometry and the automatic auscultatory methods.

Automatic oscillometry, like manual sphygmomanometry, utilizes an external inflatable cuff and is based on the measurement of air pressure oscillations induced in the pressure cuff during cuff deflation due to the cardiac activity. In automatic oscillometry, the mean blood pressure (MBP), systolic blood pressure (SBP) and the diastolic blood pressure (DBP) values are determined from the envelope of the oscillometric curve (i.e., air pressure pulse amplitudes versus cuff air pressure curve) using empirical criteria (G. Drzewiecki, "Noninvasive assessment of arterial blood pressure and mechanics" In: Medical Instruments and Devices, CRC Press, 1995, and K. G. Ng and C. F. Small, "Survey of automated noninvasive blood pressure monitors", *J. Clin. Eng.* 19:452-475, 1994).

As exemplified in FIG. 1B, in automatic oscillometry the MBP may be determined as the cuff air pressure at which the maximal oscillations Mx occur (i.e., maximal peak-to-peak amplitude in a pulsatile component of the measured cuff air pressure), the SBP may be determined as a cuff air pressure above the determined MBP value at which the oscillometric curve exhibit maximal derivative or has some predetermined percentage of the maximal amplitude (e.g., 60%), and the DBP can be derived from the same curve as a cuff pressures below the determined MBP, using similar empirical criteria. The algorithms for the determination of the SBP and the DBP from the oscillometric curve differ from one manufacturer to another. In FIG. 1B the criterion for determining the SBP and DBP is 60% and 80% of the maximal oscillometric amplitude Mx, respectively.

These empirical criteria are the main source of error in the oscillometry-based NIBP meters since the envelope of the oscillometric curve does not depend merely on the MBP, SBP and the DBP values, but also on the characteristics of the arteries under the cuff and also on characteristics of the cuff itself. It should be noted that the oscillometric pulses also appear for cuff air pressure above the SBP value, even though the arteries under the pressure cuff are closed, due to the systolic impact of the arterial blood on the tissue under the proximal (upstream) end of the cuff.

The auscultation methods are based on identifying the commencement of the Korotkoff sounds in the cuffed limb when the cuff air pressure decreases below the SBP value and the arteries under the pressure cuff are open. The automatic auscultatory methods detect the Korotkoff sounds using electronic sound-transducer and present the blood pressure readings on a digital display. However, the automatic auscultation method is prone to artifacts mainly due to external noise and vibrations.

The accuracy of the available automatic NIBP meters used at present is low, as can be deduced from the standards imposed by the Association for the Advancement of Medical Instrumentation (AAMI) and the British Hypertension Society (BHS). Both standards are based on comparing blood pressure values obtained in simultaneous measurements by the automated NIBP meter and manual Korotkoff-based sphygmomanometry (the reference standard) on subjects of wide range of blood pressure. According to both standards a device for which 5% of the examinations differ from the reference device by 15 mmHg or more is acceptable. Such low accuracy is permitted because the known methods are not capable of providing automatic blood pressure measurements of higher accuracy.

The low accuracy of oscillometry is of particular obstacle in newborns, and in particular preterm, where Korotkoff sounds are faint, or altogether absent, and manual sphygmomanometry is not always suitable for accurate assessment of the blood pressure. In newborns, the common method for the measurement of blood pressure is oscillometry, despite its low accuracy.

In photoplethysmography (PPG)-based measurement techniques a pressure cuff is wrapped around a limb of a subject and a distal PPG sensor is attached to the finger downstream to the cuff. The measured PPG signals are indicative of changes in light transmission through the tissue downstream to the location of the cuff due to the increase of arterial blood volume during the systolic (heart contraction) period and its decrease during the diastolic (heart relaxation and dilatation) period. The cuff air pressure is raised to above the SBP, and thereafter the cuff air pressure is slowly released. For cuff air pressure above the SBP, the artery under the cuff location is closed during the whole cardiac cycle, and therefore the distal PPG pulses disappear. At cuff air pressure values below the SBP, blood can pass through the artery under the cuff during that part of the cardiac cycle in which the arterial blood pressure is higher than the cuff air pressure. Thus, the systolic blood pressure may be determined from the value of the cuff air pressure at which the PPG pulses reappeared in the arteries downstream to the cuff.

As shown in FIG. 1C, the problem with the PPG-based methods is that at cuff air pressure values slightly below the SBP (23r), the measured PPG pulses are often of small amplitude (very weak), since blood can pass through the artery under the cuff only during small part of the cardiac cycle.

The SBP is determined from the cuff air pressure at which the PPG pulses reappeared during cuff deflation. However, it has been found that when the cuff is inflated at high rate, 10-20% of subjects show no pulses in the light transmission curve until the pressure has decreased significantly beyond the actual SBP (as measured by Korotkoff sounds). This effect originates from the collapse of the finger arteries under the PPG sensor downstream to the cuff due to their drainage into the veins when the cuff air pressure is above the SBP. In some cases the small blood volume pulses entering the arteries distal to the cuff when the cuff air pressure is slightly below the SBP value cannot open the collapsed arteries under the sensor.

A possible solution to this phenomena is described in U.S. Pat. No. 6,402,696, co-invented by the inventor of the present application, that proposes to reduce the drainage of blood from the arteries by increasing the cuff pressure during the cuff inflation to above the SBP value in a relatively slow rate, in order to avoid drainage of the blood from the arterial circulation and prevent possible collapse of the small arteries.

U.S. Pat. No. 7,544,168 (Nitzan 2009) and Nitzan et al. ("*Automatic noninvasive measurement of systolic blood pressure using photoplethysmography*". BioMedical Engineering OnLine, 8:28, 2009) present an automatic SBP measurement technique, which is based on PPG signal detection during pressure cuff deflation.

U.S. Pat. No. 7,544,168, co-invented by the inventor of the present application, discloses cuff-based method for improving the detection of the PPG pulses at cuff pressures slightly below the SBP, by using two PPG sensors, one of which being located distal to the pressure cuff and the other not distal to it. The former PPG sensor is used to detect the reappearance of the PPG signals when the cuff air pressure decreases below SBP value, and the role of the latter PPG sensor is to define time segments during which a PPG pulse would be expected to occur in the output of the distal-to-the-cuff detector, accounting for the time delay in the PPG signal distal to the pressure cuff (as explained by Nitzan et al., "*Effects of external pressure on arteries distal to the cuff during sphygmomanometry*" IEEE Tr. BME. 52:1120-1127, 2005). The technique also includes a decision algorithm for automatic determination whether the signal which appeared in the output of the distal-to-the-cuff detector during the time segments defined by the second sensor, is in fact a PPG signal or is a noise in the light transmission curve. The decision algorithm is also described in a paper by Nitzan et al. "*Automatic noninvasive measurement of systolic blood pressure using photoplethysmography*". BioMedical Engineering OnLine, 8:28, 2009. (U.S. Pat. No. 7,544,168B2, Nitzan 2009, Measuring systolic blood pressure by photoplethysmography).

The PPG signal in the fingers, toes, hands and feet generally has high signal-to-noise ratio when measured in a limb free of pressure cuff, but has often only small amplitude in the PPG pulses appearing at cuff pressures slightly below the SBP value, (when the artery is open for only a short time during the cardiac cycle). The small amplitude of the first PPG pulses makes it difficult to reliably differentiate the reappearance of the PPG pulses from the background noise in the light transmission curve.

US patent publication No. 2014/0142434, of the same inventor hereof, suggests a combination of two or more techniques, and suitable selection of light wavelengths, for increasing SBP measurement accuracy.

General Description

The three cuff-based methods for the determination of the SBP, DBP and MBP based on Korotkoff sounds, PPG signals or oscillometry pressure pulses, use rapid inflation of the pressure cuff to above SBP value, slow deflation of the pressure cuff and measurement, during deflation period, of a signal which is related to the blood pressure pulse (hereinafter blood-pressure-pulse related signal). Detection of an event occurring in the measured blood-pressure-pulse related signal (hereinafter blood-pressure-pulse related event) during the deflation is indicative that the corresponding cuff air pressure is equal to the SBP, DBP or MBP value of the examined subject. In the above-mentioned cuff-based techniques, the blood-pressure-pulse related event used for determining the blood pressure parameter, SBP, DBP or MBP, is obtained in a single blood-pressure-pulse. In addition, each blood pressure parameter, SBP, DBP or MBP, determined in these methods is associated with a different blood-pressure-pulse.

Since the blood pressure parameters, SBP, DBP and MBP change from pulse to pulse (i.e. blood pressure variability, in the respiration frequency and in lower frequencies), the single measured value of SBP, DBP or MBP in each of the three cuff-based methods cannot reliably represent the average value of SBP, DBP or MBP in the arterial blood of the person undergoing blood pressure measurement. There is a need in the art for automatic and non-invasive pressure cuff-based measurement of clinically-important parameters of arterial blood pressure, such as SBP, DBP and MBP, to obtain more representative values of the blood pressure parameters. The present application provides techniques and sensor configurations capable of measuring arterial blood pressure parameters with substantially improved accuracy relative to the available blood pressure meters, by using reference measurement data of blood-pressure-pulse related signal measured (e.g. by means of a PPG sensor or tonometer) in a body part not affected by the cuff pressure, that can be used as a surrogate for the assessment of beat-to-beat blood pressure variability and for obtaining more representative value of SBP, DBP or MBP from the single measured value of the blood pressure parameters.

The inventor of the present invention devised techniques for determining average values of SBP, DBP and/or MBP in several pulses, providing more representative values of the blood pressure parameters than those obtained in a single blood pressure pulse. This is achieved, in some embodiments, by simultaneously conducting measurements of blood-pressure-pulse related signal in two different body parts/organs of the examined subject, where one of the measurements being conducted in a body part (hereafter pressure-affected body part) in or downstream to a site to which descending pressure conditions are being applied (e.g., a limb or other organ of the subject), and the other measurement being conducted in a body part/region to which the pressure conditions are not being applied (hereafter pressure free body part e.g., another limb/organ of the subject).

In some embodiments the measurements conducted in the pressure-affected body part comprise oscillatory air pressure measurements (e.g., using oscillometric pressure sensor), optical measurements (e.g., using a PPG sensor), Doppler velocimetry measurements (e.g., using ultrasonic Doppler velocimeter or laser Doppler flowmeter), and/or Korotkoff sounds measurements (e.g., using a stethoscope or an acoustic signal sensor), and the measurements conducted in the pressure-free body part comprise optical measurements and/or pressure changes measurements (e.g., arterial tonometry). In the embodiments disclosed herein, the instantaneous whole value of the air pressure applied over the pressure-affected body part, relative to zero air pressure, (hereinafter absolute air pressure value) is also being simultaneously measured during cuff deflation, in order to determine the value of the air pressure at which a blood-pressure-pulse related event is identified.

The measurements obtained from the pressure-affected body part are used to determine a point in time at which a blood-pressure-pulse related event is identified therein, which occurred responsive to the applied descending pressure conditions. The determined point in time is then used to determine the absolute air pressure level applied over the pressure-affected body part when the blood-pressure-pulse related event occurred therein (referred to herein as initial blood pressure parameter value), and to determine from the measurements obtained from the pressure-free body part a correction factor for the determined value of the initial blood pressure parameter, in order to provide more representative/ accurate SBP, DBP and/or MBP measurement for the examined subject.

In one embodiment the blood-pressure-pulse related signal measurements taken from the pressure-affected body part are the cuff air pressure oscillations associated with the arterial blood pressure oscillations, which change according to the instantaneous absolute air pressure applied on the pressure-affected body part. For example, and without being limiting, the blood-pressure-pulse related event may be the maximal amplitude air pressure oscillation measured, being indicative of an initial MBP value. Similarly a suitable derivative of the oscillatory curve can be used for the derivation of an initial SBP value or as an initial DBP value.

If optical measurements are used in the pressure-affected body part, then the blood-pressure-pulse related event is preferably the appearance of PPG pulses in the measured optical signal, in case descending pressure conditions are being applied, indicating that the instantaneous absolute air pressure value is equal to the initial SBP value. In case ascending pressure conditions are being applied the disappearance of the pulsations indicate that the instantaneous absolute air pressure value is equal to the initial SBP value. Similarly, if acoustic measurements are taken from the pressure-affected body part for the measurement of SBP, then the blood-pressure-pulse related event is the appearance of the Korotkoff sounds, in case descending pressure conditions are being applied, or the disappearance of the Korotkoff sounds, in case ascending pressure conditions are being applied. For the measurement of DBP the suitable events are the disappearance of the Korotkoff sounds, in case descending pressure conditions are being applied, and the appearance of the Korotkoff sounds, in case ascending pressure conditions are being applied.

In the above-mentioned cuff-based methods for the measurement of SBP, DBP and MBP, the blood-pressure-pulse related event is indicative of an initial blood pressure parameter value determined from the instantaneous absolute pressure measurements being simultaneously conducted in the pressure-affected body part. The time at which the blood-pressure-pulse related event occurred in the pressure-affected body part is also used as a time indication in the processing of the reference measurement data obtained from the blood-pressure-pulse related signals measured in the pressure-free body part.

In some embodiments the measurements conducted in the pressure-free body part are optical measurements in which tissue region of the body part is illuminated with light in the visible or infrared regions, and light transmitted through, and/or reflected from, the tissue is measured (e.g., using a PPG sensor). The time indication determined from the measurements in the pressure-affected body part can be used to define a time window centered thereabout for the processing and analysis of the blood-pressure-pulse related-signals obtained from the pressure-free body part. The time window may be based on a predetermined time interval (e.g., of about 5 to 30 seconds) centered about the determined time indication, or, based on a predefined number of measured blood-pressure-pulse related pulses to be processed and analyzed for determining the correction factor.

For example, and without being limiting, the time indication of the occurrence of the blood-pressure-pulse related event in the pressure-affected body part can be used to identify in the measurements conducted in the pressure-free body part a blood-pressure-pulse related signal pulse (e.g., PPG or air pressure pulse) measured therein at the time the blood-pressure-pulse related event occurred at the pressure-affected body part. Optionally, and in some embodiments preferably, the time window is defined to consist of 2N+1 (where N is a positive integer in range of 2-15) blood-pressure-pulse related signal pulses measured in the pressure-free body part and centered about the blood-pressure-pulse related signal pulse measured therein at the time the blood-pressure-pulse related event occurred at the pressure-affected body part. In this case, the 2N+1 blood-pressure-pulse related signal pulses of the time window are processed and analyzed to determine the correction factor for computing the average blood pressure parameter (e.g. SBP) value to be determined for the examined subject.

In some embodiments the correction factor is determined using a characteristic parameter (e.g., maximum, minimum, or amplitude) of the blood-pressure-pulse related signal measured in the pressure-free body part within the time window. Preferably, the correction factor is the ratio between the average (the arithmetic mean) of the characteristic parameter of the blood-pressure-pulse related signal measured within the time window and the value of the characteristic parameter of the blood-pressure-pulse related signal measured in the pressure-free organ when the blood-pressure-pulse related event occurred in the pressure-affected body part.

In some embodiments descending pressure conditions are applied (e.g., by a pressure cuff) over the pressure-affected body part of the examined subject, starting from a pressure level greater than the SBP, while conducting therein blood-pressure-pulse related signal measurements associated with at least one of the SBP, DBP or MBP of the subject, and generating measurement data indicative thereof. At the same time of applying the descending pressure conditions and conducting the blood-pressure-pulse related signal measurements, blood-pressure-pulse related signal measurements are also conducted in the pressure-free body part, and measurement data indicative thereof is generated, while simultaneously generating pressure data indicative of the measured instantaneous absolute air pressure that is being applied over the pressure affected body part.

The reference measurement data measured in the pressure-free body part is then processed and analyzed to determine a pulsatile component thereof. The measurement data measured in the pressure-affected body part is processed and analyzed to identify a blood-pressure-pulse related event related to the SBP, DBP or MBP of the subject, and a point in time in which the blood-pressure-pulse related event had occurred therein. The determined point in time of the occurrence of the blood-pressure-pulse related event is then used for determining in the air pressure data an air pressure level applied over the pressure-affected organ at the time the blood-pressure-pulse related event occurred in the pressure-affected body part, and to identify in the reference measurement data measured in the pressure-free body part a blood-pressure-pulse related signal pulse that occurred at the time at which the blood-pressure-pulse related event had occurred in the pressure-affected body part.

The determined absolute air pressure level at the time the blood-pressure-pulse related event occurred in the pressure-affected body part is used to determine an initial SBP, DBP or MBP, value of the subject. A group of consecutive blood-pressure-pulse related signals measured in the pressure-free body part, including and centered about the blood-pressure-pulse related signal measured at the time the blood-pressure-pulse related event occurred, is selected, and then for each blood-pressure-pulse related signal in the selected group a characteristic parameter is determined (e.g., baseline or amplitude of each blood-pressure-pulse related signal pulse). It is noted that such characteristic parameter spontaneously changes in the measured blood-pressure-pulse related signals, and that these changes are in correlation with the spontaneous change of the SBP, DBP or MBP of the examined subject. (see "*The very low frequency variability in the arterial blood pressure and in the blood volume pulse.*" by Nitzan et al, 1999, *Medical and Biological Engineering and Computing vol.* 37, pp 54-58.)

The characteristic parameter of the blood-pressure-pulse related signals in the selected group of consecutive blood-pressure-pulse related signals is then used to determine a correction factor for the initial SBP, DBP or MBP value. In some embodiments an average of the characteristic parameter determined for the blood-pressure-pulse related signal pulses in the selected group of blood-pressure-pulse related signal pulses is computed and used to compute an average-to-single ratio between the computed average of characteristic parameter and the characteristic parameter of the blood-pressure-pulse related signal pulse occurred when the blood-pressure pulse related event occurred in the pressure-affected body part. An average SBP, DBP or MBP of the examined subject is then evaluated by multiplying the initial SBP, DBP or MBP value with the computed average-to-single ratio.

In some embodiments optical measurements are performed in both the pressure-affected and pressure-free body parts of the examined subject, and respective optical data is measured in each of the body parts during application of the descending (or ascending) pressure conditions. In this case, the optical data measured in the pressure-affected body part is processed and analyzed to determine optical data components comprising a pulsatile component (at the heart-rate) and/or a slowly changing component (hereinafter DC or baseline component). At least one of the optical data components is then processed and analyzed to identify a blood-pressure-pulse related event therein indicative that the pressure applied over the pressure-affected body part is smaller than a SBP of the examined subject (i.e., indicative of systolic increase of blood volume in the tissue downstream the pressure-affected region), and the point in time in which the blood-pressure related event occurred.

The point in time at which the blood-pressure-pulse related event occurred in at least one of the optical data components (i.e. pulsatile or DC component) is then used to determine from the air pressure data the absolute air pressure value applied over the pressure-affected body part when the blood-pressure-pulse related event occurred (e.g., a maximal applied cuff air pressure at which changes associated with the specific component appeared), and from the optical data measured in the pressure-free body part a blood-pressure-pulse related signal pulse that occurred at that same time. The air pressure level determined at the time the blood-pressure-pulse related event occurred is used as the initial SBP value. The determined initial SBP value and the determined blood-pressure-pulse related signal occurred in the pressure-free body part when the blood-pressure-pulse related event occurred are then used to evaluate the average SBP in a similar manner as described hereinabove.

More particularly, a group of 2N+1 consecutive heart pulse signals measured in the pressure-free body part, including and centered about the blood-pressure-pulse related signal pulse occurred in the pressure-free body part at the time at which the blood-pressure-pulse related event (i.e., associated with the pulsatile or DC component) occurred, are selected i.e., including N blood-pressure-pulse related signal pulses measured before the event and N blood-pressure-pulse related signal pulses after the event. For each blood-pressure-pulse related signal pulse in the selected group of blood-pressure-pulse related signal pulses a characteristic parameter is selected, and an average of the characteristic parameter of the 2N+1 blood-pressure-pulse related signal pulses is used to compute the respective average-to-single pulse ratio, as described hereinabove. The computed average-to-single pulse ratio is then similarly used to evaluate the average SBP of the examined subject, by multiplying the average-to-single ratio by the initial SBP value determined for the examined subject.

In some embodiments the initial SPB value of the examined subject is determined based on the instantaneous absolute air pressure values at which the PPG volumetric bloodflow related changes started to appear in one of the pulsatile and DC components determined for the optical data measured in the pressure-affected body part. In other words, in some embodiments, the initial SBP value is determined to be the instantaneous absolute air pressure applied over the pressure-affected body part at the time in which a change indicative that the applied pressure declined to a level smaller than the SBP of the examined subject was identified by change in one of the pulsatile and DC components of the PPG signals measures therein. The determined initial SBP value is multiplied by the average-to-single pulse ratio in order to provide more representative assessment of the SBP of the examined subject from single SBP measurement to an averaged SBP measurement.

For better understanding of the invention a brief description of some principles and terms is provided in the sections below. FIG. 2 shows a PPG signal 10 measured in a finger (also referred to herein as examined tissue) of a subject in limb free of pressure cuff (i.e., no pressure is applied over the limb). As seen in FIG. 2 the light transmission through the examined tissue varies over time, which reflects blood volume variations in the arteries in the examined tissue. In the PPG-signal 10 the maximal intensity of transmitted light, $I_D$, occurs at the end of the diastolic phase (10*x*, when the tissue blood volume is at minimum), and the intensity of transmitted light decreases during the systolic phase (when tissue blood volume increases) and reaches a minimum, Is, occurring at the end of the systolic phase (10*n*). Accordingly, a PPG pulse may be defined as the PPG signal persisting in the time region 10*t* between consecutive maximums 10*x*. The DC value for each PPG pulse (also referred to herein as DC value or baseline value), may be defined as: (i) the minimum measured light intensity $I_S$ of the PPG pulse; (ii) the maximum measured light intensity of the PPG pulse $I_D$; or (iii) an average value of measured light intensity of the PPG pulse, during the PPG pulse period. The DC component (also referred to herein as baseline component or trend) of the PPG signal is defined in some embodiments as the light transmission curve after the application of a low-pass filter (such as an electronic RC circuit or digital moving average filter) that filters out the PPG pulses (a pulsating component in the heart rate of the measured signal). The AC component (also referred to herein as pulsatile component) of the PPG signal is the PPG signal after subtracting the DC component from the measured PPG signal. The amplitude of the PPG pulse may be generally defined by $I_D$-$I_S$ i.e. by the subtraction of the minimal (systolic) intensity in the AC component from the maximal (diastolic) intensity. Both DC and AC components of the PPG signal have spontaneous fluctuations, which are correlated with the SBP and DBP spontaneous fluctuations.

FIG. 3A shows a typical PPG signal reflecting the variability of the measured PPG signals. FIG. 3B shows the variability of the $I_D$ and $I_S$ values of the PPG signal, and FIG. 3C shows its amplitude variability.

FIG. 1C shows a PPG signal 21 in a finger distal/downstream to a pressure cuff wrapped around an arm of an examined subject and a curve 20 of the pressure in the cuff. For cuff air pressure above the SBP value the PPG signal disappears (at 23d), and reappears when the cuff pressure decreases below the SBP value (at 23r). It should be noted, however, that at cuff pressures slightly below the SBP, the artery under the cuff is closed in most of the cardiac cycle, and is open only when the arterial blood pressure increases above the cuff pressure. Thus, as shown in FIG. 1A, only small amount of blood can pass through the arteries downstream to the cuff in each heartbeat, thereby generating small pulses in the light transmission curve (i.e., the gray filled portion of the pulses in FIG. 1A). The time at which the cuff pressure decreased to the SBP value, as determined by sphygmomanometry ($SBP_S$) is marked by a bold line identified by numeral reference 22 in FIG. 1C. In several cases the PPG pulses 21w occurring shortly after the decrease of the cuff pressure below the $SBP_S$ 23r cannot be undoubtedly detected since their amplitude is in the range of the background noise.

FIG. 4 and FIG. 5 present raw light transmission curves for an adult (31, in FIG. 4) and for a neonate (41, in FIG. 5), respectively, during the decrease of cuff pressure, measured by a PPG probe (e.g., comprising a light source and light detector optically coupled to the examined tissue) downstream to the cuff after raising the cuff pressure to a pressure above the SBP value and gradually releasing the cuff pressure to a pressure below the SBP. In both examples the light transmission gradually decreases after the cuff pressure decreases below the SBP value. The time at which the cuff pressure decreased to the value of the SBP, as obtained by auscultatory sphygmomanometry is identified in FIG. 4 by asterisk 33, and in FIG. 5 by arrow 43 as obtained by oscillometry. The decrease of light transmission is due to the gradual increase of blood volume in the pressure-affected organ, due to entrance of arterial blood during systole without draining by the veins, which are closed by the cuff.

The DC component (trend) of the light transmission curve is obtained by smoothing the light transmission curve over several pulses, so that the PPG pulses are eliminated. After subtraction of the trend of the light transmission curves from the light transmission curves themselves, and magnifying the scales, it is possible to see more clearly the PPG pulses, when the cuff air pressure decreased below the SBP value. These PPG pulses can be seen in the AC curve 36 shown in FIG. 4 for an adult, and in the AC curve 46 shown in FIG. 5 for a neonate. Both the decrease in the light transmission curves and the reappearance of the PPG pulses in the AC curves when the cuff pressure decreases below the SBP value can be used for the determination of the SBP value for the examined subject/neonate. However, the PPG pulses measured at cuff pressures slightly below the SBP are small and faint, and in many cases it is difficult to detect them on the background of noise in the AC curve. For the same reason the decrease in the light transmission curves at cuff pressures slightly below the SBP is small, and in many cases it is difficult to detect it on the background of low frequency noise in the light transmission curve.

FIG. 4 and FIG. 5 also show the PPG curves obtained by a second PPG probe attached to cuff-free (pressure free) organ of the examined adult/neonate. More particularly, curve 38 in FIG. 4 shows cuff-free PPG signals obtained from a finger in the other hand of the (adult) subject, and curve 48 in FIG. 5 shows cuff-free PPG signals obtained from the other foot of the neonate. These cuff free PPG signals are used in some embodiments as a time reference to more accurately identify time regions in which the PPG pulses distal (downstream) to the cuff were expected to reappear.

The vertical dashed lines (35 and 45 in FIG. 4 and FIG. 5, respectively) show the start of the decrease in the systolic pressure in the PPG pulses measured in the limb free of cuff pressure. As seen, the PPG pulses distal to the cuff appear with time delay At relative to those in the cuff-free organ. This delay At results from changes in the hemodynamic properties of the arteries under the cuff or distal to the cuff as a result of the inflation and deflation of the cuff, and has to be considered when determining the time regions in which the PPG pulses distal (downstream) to the cuff are expected to reappear.

The cuff-free PPG signals are used in some embodiments for the assessment of the average SBP from the single (initial) SBP measurement, which is derived from the cuff absolute air pressure value when the first PPG signal reappeared. Curve 38 in FIG. 4 and curve 48 in FIG. 5 show cuff-free PPG signals and also show the variability in the baseline and amplitude of the cuff-free PPG signals. The average value of the baseline or the amplitude of the PPG signal is used in some embodiments for the assessment of the average SBP value of the subject.

The variability of the PPG signal originates from sympathetic nervous activity and is therefore a measure to the sympathetic nervous activity. In particular the standard deviation of one of the characteristic parameters ($I_D$, $I_S$ or $I_D$-$I_S$) is a measure to the sympathetic nervous activity. The latter is a physiologic parameter which is strongly related to blood pressure, and has therefore clinical significance. In some embodiments the variability of the PPG signal in the pressure-free body part can be used for the assessment of the sympathetic nervous activity.

In some embodiments, the detection of the decrease (i.e., change in the trend of the DC curve from monotonic increase towards monotonic decrease) in the DC light transmission curve is preferable to the detection of the PPG pulses in cases of noise in the frequency range of the cardiac cycle, i.e., 0.5-3 Hz (the existing frequency range of the PPG pulses), but has lower reliability in these cases where the light transmission curve has noise fluctuations of lower frequency. Similar to the reappearance of the PPG pulses, at cuff pressures slightly below the SBP the magnitude of the rate of decrease in the DC light transmission curve is small, since blood can pass through the arteries under the cuff only during small part of the cardiac cycle.

In possible embodiments two PPG probes are respectively utilized to measure the blood-pressure-pulse related signals in the pressure-affected body part and in the pressure-free body part. Each such PPG probe typically comprises a light detector (e.g., PIN diode) and at least one light source (e.g., LED) configured to illuminate the examined tissue with light of at least one predetermined wavelength e.g., in the infrared spectrum. The light source may be configured to operate in a transmission-mode (e.g., finger probe 70 as exemplified in FIG. 8), or placed at a distance of about 5 to 20 millimeters from the detector in a reflection-mode arrangement (e.g., foot probe 80 as exemplified in FIG. 9). This light sources and light detectors of the PPG probes can be operated by a control unit in conjunction with a pressure device, as described herein above and below, wherein the control unit is configured and operable to actuate the light sources, receive optical data indicative of passage of the illuminated light through the examined tissues in the pressure-affected and in the pressure-free body parts, as measured by the respective light detectors, and air pressure data indicative of the pressure applied over the pressure-affected body part by the pressure device, and process and analyze the optical and air pressure data to determine the one or more blood pressure indications of the examined subject using one or more of the techniques described herein.

In possible embodiments identifying a change in pulsatile component of the measured optical data (e.g., reappearance of the PPG pulses) is carried out using one or more suitable algorithms (e.g., as described in U.S. Pat. No. 7,544,168 and/or by Nitzan et al, in "*Automatic noninvasive measurement of systolic blood pressure using photoplethysmography*", *BioMedical Engineering OnLine*, 8:28, 2009), configured to detect PPG pulses in a slowly changing signal.

In some embodiments the detection of the changes in the pulsatile and baseline components of the light transmission curves is carried out visually by offline inspection of the light transmission curves, and single-pulse (initial) SBP value of the subject is determined from the value of the cuff pressure at the time of the detection of the PPG pulses in the pulsatile component, or the commencement of declination in the baseline component. In these techniques the average SBP is determined by multiplying the single-pulse SBP value by the average-to-single ratio.

In some embodiments the rate of change of the applied descending/ascending pressure conditions is set in the range of 1 to 5 mmHg/sec, preferably about 1 to 2 mmHg/sec, in order to increase the accuracy of the pressure measurement.

In some embodiments, when descending pressure conditions are being applied over the pressure-affected body part, the pressure applied by the pressure device is raised to above the SBP value in relative slow rate, in the range of 10 to 15 mmHg/sec, in order to avoid drainage of the blood from the arterial circulation and possible collapse of the small arteries.

In some embodiments the signal-to-noise ratio (SNR) of measured PPG signals is increased by inducing in the examined tissue conditions resembling reactive hyperemia. Reactive hyperemia is the transient increase in organ blood flow that occurs following a brief period of arterial occlusion and stop of blood flow (ischemia). The hyperemia occurs because during the period of occlusion, tissue shortage of oxygen supply and a buildup of $CO_2$ concentration in the tissue dilate arterioles and increase vascular compliance. The longer the period of occlusion, the greater the metabolic stimulus for vasodilation leading to increases in arterial dilatation. The effect of myogenic mechanism also contributes to reactive hyperemia: the arterial occlusion results in a decrease in blood pressure downstream in arterioles, which can lead to myogenic-mediated vasodilation. Reactive hyperemia can be used for increasing the SNR of the PPG signal and consequently for the increase of the accuracy of the PPG-based SBP measurement technique.

Accordingly, in some embodiments the inflation of the pressure cuff to an air pressure above the SBP value is not immediately followed by deflating the cuff and decreasing the air pressure, but the cuff air pressure is maintained at a value above the SBP value (arterial occlusion pressure) for at least 1 minute in order to induce increased blood flow in the pressure-affected body part after the pressure applied thereover is reduced below the SBP (as in reactive hyperemia). The resultant arteriolar dilation increases the blood flow during systole and the amplitude of the measured PPG signals. Optionally, and in some embodiments preferably, the cuff air pressure is maintained at a value above the SBP value up to 5 minutes.

In some embodiments the PPG probe used in the pressure-free organ is utilized to simultaneously obtain PPG signals from a tissue site in which the blood circulation is not affected by the cuff pressure (e.g., in a contralateral limb or upstream the cuff) used as a time-reference for the differentiation of the reappearance of the PPG pulses from background noise. Alternatively, or additionally, pressure pulses in the cuff or an ECG R-wave may also be used as a time-reference for the start of a heart-induced pulse.

In some embodiments the initial SBP value is determined by the PPG-based technique based on identification of a single PPG pulse that was the first to be detected during cuff deflation, and the initial DBP is determined by the Korotkoff sounds identification technique in a single Korotkoff sound pulse identification (or by the oscillometry method). The average DBP and SBP can be then computed using the respective 2N+1 pressure pulses e.g., if tonometry is used, or 2N+1 optically measured pulses e.g., if a PPG sensor is used, measured from the pressure-free body part, as described hereinabove and hereinbelow. The initial DBP and SBP values are then multiplied by the ratio of the average of the minimum values ($I_S$) of the 2N+1 pressure pulses and the minimum value ($I_S$) of the pulse measured in the pressure-free body part when the blood-pressure-pulse related event occurred in the pressure-affected body part, in order to obtain the respective average DBP and the SBP values.

Similar correction factor can be applied to the single DBP determined by using the maximum values of the PPG pulse signals ($I_D$), or the amplitudes of the PPG pulse signals ($I_D$-$I_S$), of the 2N+1 pulses measured in the pressure-free body part.

In some embodiments the initial mean blood pressure of the examined subject is measured by the oscillometry method by identifying the air pressure pulse of maximal amplitude measured in the air pressured cuff, which appears when the instantaneous absolute cuff air pressure is equal to the value of mean blood pressure, as described hereinabove with reference to FIG. 1B. In order to assess the average mean blood pressure of the examined subject, a correction factor is computed using characteristic parameter (e.g., signal minimum $I_S$, maximum $I_D$, or its amplitude $I_D$-$I_S$) of the sequence of 2N+1 pulses measured (e.g., optically measured by PPG, or pressure pulses measured by a pressure transducer) in the pressure-free organ, including and centralized about the time at which the pressure pulse of maximal air pressure occurred in the pressure-affected organ. Optionally, the correction factor is an average-to-single pulse ratio computed for the sequence of 2N+1 oscillometry pressure pulses. The mean blood pressure value of the examined subject is then multiplied by the correction factor to determine the average mean blood pressure of the examined subject.

In some embodiments the initial SBP or DBP value of the examined subject is determined using the oscillometric technique in the corresponding single air pressure pulse identification scheme illustrated in FIG. 1B i.e., based on the air pressure pulse, or some fraction of the air pressure pulse, of maximal amplitude measured in the air pressured cuff (or another empirical criterion). In order to assess the average SBP or DBP 2N+1 pressure pulses or light transmission pulses measured in the pressure-free body part are used to compute the correction factor (average-to-single ratio), and the initial SBP or DBP value is then multiplied by the computed correction factor. Optionally, the correction factor is computed using the average value of the minimum values ($I_S$) of the 2N+1 pressure pulses measured in the pressure-free body part.

Similarly, the correction factor can be applied to the initial MBP values obtained by means of oscillometry measurements in the pressure-affected body part, by using the maximal PPG pulses parameter ($I_D$), or the amplitude of the PPG pulses ($I_D$-$I_S$), of the 2N+1 PPG pulses measured in the pressure-free body part.

In some possible embodiments the initial SBP is determined based on identification of the first (reappearing) blood-pressure-pulse related signal detected during the cuff deflation, and the initial MBP is measured by the oscillometric method by identifying the single cuff air pressure pulse of maximal amplitude as described hereinabove with reference to FIG. 1B. A PPG sensor or a pressure transducer (directly placed over an artery, or connected to a pressure-cuff wrapped round a limb) can be used to obtain the blood-pressure-pulse related signals in the pressure-free body part used to determine simultaneously the correction factor for computing the average SBP and MBP of the examined subject (using the 2N+1 optical or pressure pulses to compute the correction factor, as described hereinabove, and multiplying the correction factor by the values determined as initial SBP and MBP). The value of DBP can be obtained in some embodiments from the values of SBP and MBP by the equation MBP=(2DBP+SBP)/3 i.e., by computation of DBP=(3*MBP−SBP)/2.

In some embodiments descending pressure conditions are applied over the pressure-affected body part starting from a pressure greater than the SBP, while simultaneously conducting optical (e.g., PPG) measurements therein. Accordingly, when the descending pressure conditions are being applied, the instantaneous absolute air pressure data is processed to determine a highest pressure value at which at least one of the pulsatile and baseline components of the optical measurement exhibits changes associated with increase of blood volume in the pressure-affected body part. The highest pressure value from the pressure values determined for the pulsatile and baseline components is then used as the initial blood pressure value of the subject for which a correction factor is computed from measurements taken from the pressure-free body part of the subject, as described hereinabove and hereinbelow, to determine the respective average blood pressure value.

In some embodiments ascending pressure conditions are applied over the pressure-affected body part, starting from a pressure smaller than the systolic blood pressure, while simultaneously conducting optical (e.g., PPG) measurements therein. Accordingly, when the ascending pressure conditions are being applied, the pressure data is processed to identify a highest pressure value at which at least one of the pulsatile and baseline components of the optical measurement exhibits changes associated with increase of blood volume in the pressure-affected body part, which is then similarly used as the initial blood pressure value of the subject.

In some applications the system includes a sound transducer configured and operable to sense acoustic/audible signals in the pressure-affected body part while the changing absolute air pressure conditions are being applied and generate audible data indicative thereof, wherein the control unit is configured to process the audible data and detect Korotkoff sounds therein. These Korotkoff sounds detection techniques may be used to determine the initial SBP and/or DBP in one or more of the embodiments disclosed herein. For example, if ascending pressure conditions are being applied over the pressure-affected body part, the pressure data can be processed to determine the initial SBP as the pressure at which the Korotkoff sounds in the pressure-affected body part disappeared, and determine the initial DBP as the minimum air pressure value which still demonstrates the Korotkoff sounds. An optical probe or a pressure transducer adapted to conduct blood-pressure-pulse related signals in the pressure-free hand can be then used to compute the correction factor as described herein above and below.

In one aspect there is provided a system for determining average value of an arterial blood pressure parameter (e.g., SBP, DBP and/or MBP) of an examined subject. The system comprising a pressure device configured and operable to apply changing pressure conditions over a body part of the subject, and generate pressure measurement data indicative of the pressure applied over the body part by the pressure device, a first measuring unit configured and operable to measure blood-pressure-pulse related signals in the pressure-affected body part (under or distal to the pressure device) and generate blood-pressure-pulse related measurement data indicative thereof, a second measuring unit configured and operable to measure blood-pressure-pulse related signals in a pressure-free body part of the examined subject and generate reference blood-pressure-pulse related measurement data indicative thereof, and a control unit configured and operable to operate the pressure device to apply the changing pressure conditions over the pressure-affected body part and simultaneously operate the first and second measuring units, determine an initial blood pressure parameter value of the subject based on the measurement data from the pressure device and from the first measuring unit, determine a correction factor based on the measurement data from the second measuring unit and from the first measuring unit, and determine the average blood pressure parameter of the examined subject based on the initial blood pressure parameter value and the correction factor.

Optionally, and in some embodiments preferably, the pressure device is an air pressure cuff configured to apply the changing pressure conditions on the site under the pressure device. The changing pressure conditions are monotonic descending air pressure or monotonic ascending air pressure.

In some embodiments the control unit is configured and operable to process and analyze the pressure measurement data generated by the pressure device and the blood-pressure-pulse related measurement data generated by the first measuring unit and identify a blood-pressure-pulse related event therein associated with the applied changing pressure conditions for determining the initial blood pressure parameter value of the subject. The control unit can process and analyze the reference measurement data indicative of the blood-pressure-pulse related signals measured in the pressure-free body part within a segment of time within which the blood-pressure-pulse related event occurred in the pressure-affected body part for determining based thereon the correction factor.

For example, the control unit can determine the correction factor as the ratio of the average value of a characteristic parameter (e.g., pulse maximum, pulse minimum, pulse amplitude) of the blood-pressure-pulse related signals measured in the pressure-free body part within the time segment and the value of the characteristic parameter of the blood-pressure-pulse related signal measured in the pressure-free body part when the blood-pressure-pulse related event occurred in the pressure-affected body part. The time segment may be determined by the control unit by identifying in the reference data a blood-pressure-pulse related signal measured in the pressure-free body part at the point in time the blood-pressure-pulse related event occurred in the pressure-affected body part, and defining the time segment to include a predetermined number of heart-induced pulse signals (e.g., 5 to 31, inclusive) including and centered about the blood-pressure-pulse related signal.

The first measuring unit comprises in some embodiments at least one of the following: a PPG sensor configured and operable to measure PPG pulses in the pressure-affected body part, and generate PPG measurement data indicative thereof; an optical probe configured and operable to measure light transmission changes associated with blood-pressure-pulses in the pressure-affected body part, and generate optical measurement data indicative thereof; an acoustic sensor configured and operable to measure Korotkoff sounds, and generate acoustic measurement data indicative thereof; and a pressure sensor configured and operable to measure oscillatory air pressure changes in the pressure cuff associated with arterial blood pressure oscillations in the pressure-affected body part, and generate air pressure measurement data indicative thereof.

Optionally, and in some embodiments preferably, the pressure conditions applied by the pressure device on the pressure-affected body part are monotonically descending starting from a pressure level greater than a systolic blood pressure of the subject. In this case, the control unit identifies the blood-pressure-pulse related event in the blood-pressure-pulse related data obtained from the first measuring unit as either appearance of blood-pressure-pulse related signal in either the optical, acoustic, PPG or arterial blood pressure measurement data, or as a change in a trend of a baseline component of either the optical measurement data or the PPG measurement data.

Alternatively, the pressure conditions applied by the pressure device on the pressure-affected body part are monotonically ascending until reaching a pressure level greater than a systolic blood pressure of the subject. In this case, the control unit identifies the blood-pressure related event in the blood-pressure-pulse related data obtained from the first measuring unit as either vanishing of heart-induced pulse signals in either the optical, PPG, acoustic, or pressure, measurement data, or as a change in a trend of a baseline component of either the optical data or the PPG data. For example, and without being limiting, the arterial blood pressure parameter is MBP and the control unit is configured and operable to identify the blood-pressure-pulse related event as an air pressure pulse of maximal amplitude identified in the air pressure data.

In some embodiments the second measuring unit comprises at least one of the following: a PPG sensor configured and operable to measure PPG signals in the pressure-free body part and generate reference PPG measurement data indicative thereof; an optical probe configured and operable to measure light transmission changes associated with blood-pressure-pulses in the pressure-affected body part and generate reference optical measurement data indicative thereof; a pressure sensor configured and operable to measure arterial blood pressure changes in the pressure-free body part and generate reference pressure measurement data indicative thereof; and a pressure sensor configured and operable to measure oscillatory pressure changes associated with arterial blood pressure changes in the pressure-free body part, and generate reference oscillatory measurement pressure data indicative thereof.

Optionally, the control unit is further configured to assess sympathetic nervous activity of the examined subject, by deriving a parameter (e.g., the standard deviation of one or more of the characteristic parameters $I_D$, $I_S$ or $I_D$-$I_S$) that provides assessment of the variability of the reference blood-pressure-pulse related measurement data measured in the pressure-free body part.

In another aspect, there is provided a system for determining at least one blood pressure parameter of an examined subject, the system comprising a pressure device having a pressure applying element configured and operable to apply changing pressure conditions over a body part of the subject, and a pressure sensor configured to measure the pressure in the pressure applying element and generate pressure data indicative thereof, the pressure data comprising an operative component indicative of the pressure applied by the pressure device over the body part and a pulsating component indicative of blood-pressure-pulses of the examined subject induced into the pressure measurement; a measuring unit configured to measure blood-pressure-pulse related signals in a pressure-free body part of the examined subject, and generate reference data indicative thereof; and a control unit configured and operable to operate the pressure device to apply the changing pressure conditions over the pressure-affected body part and simultaneously operate the measuring unit, determine an initial blood pressure parameter value of the subject based on the operative and pulsating components of the pressure data, determine a correction factor based on the reference data and the pressure data, and determine the average blood pressure parameter of the examined subject based on the initial blood pressure parameter value and the correction factor.

For example, the processing unit can process and analyze the pulsating component of the pressure data to identify a blood-pressure-pulse related event therein associated with the pressure applied by the pressure applying element for determining the initial blood pressure parameter value of the subject, and process and analyze the reference data within a segment of time within which the blood-pressure-pulse related event occurred in the pressure-affected body part for determining the correction factor.

In yet another aspect there is provided a system for determining at least one blood pressure parameter (e.g., SBP, DBP and/or MBP) of an examined subject, the system comprising a pressure device configured and operable to apply air pressure conditions over a body part of the subject, and generate pressure data indicative of the pressure being applied over the body part, a measuring unit configured and operable to measure blood-pressure-pulse related signals in the pressure-affected body part of the examined subject under or distal to the pressure device, and generate blood-pressure-pulse related data indicative thereof, and a control unit configured and operable to operate the pressure device to apply over the pressure-affected body part air pressure above SBP value during a predefined time period (e.g., greater than one minute) sufficient to induce a condition causing increased blood flow in the pressure-affected body part after the pressure applied thereover is reduced below the SBP (as in reactive hyperemia conditions), and thereafter apply decreasing pressure conditions, and simultaneously operate the measuring unit, process and analyze the measured pressure data from the pressure device and the blood-pressure-pulse related data generated by the measuring unit to identify a blood-pressure-pulse related event therein associated with the applied changing pressure conditions for determining the blood pressure parameter value of the subject.

In yet another aspect there is provided a method of determining at least one blood pressure parameter (e.g., SBP, DBP and/or MBP) of an examined subject, the method comprising affecting changing pressure conditions over a body part of the subject and simultaneously performing the following steps: measuring the pressure applied over the pressure-affected body part; measuring blood-pressure-pulse related signals in the pressure-affected body part of the examined subject and generating blood-pressure-pulse related data indicative thereof; measuring blood-pressure-pulse related signals in a pressure-free body part of the examined subject and generating reference data indicative thereof; determining an initial blood pressure parameter value of the subject based on the measured pressure data and blood-pressure-pulse related data; generating a correction factor based on the reference data and the blood-pressure-pulse related data; and determining the average blood-pressure parameter value based on said initial blood pressure parameter value and said correction factor.

Optionally, and in some embodiments preferably, the determining of the initial blood pressure parameter value of the subject comprises identifying in the blood-pressure-pulse related data a blood-pressure-pulse related event associated with the pressure applied over the pressure-affected body part and determining the initial blood pressure parameter value of the subject according to the pressure applied on the pressure affected body part when said blood-pressure-pulse related event occurred. Generation of the correction factor comprises in some embodiments processing a segment of the reference data associated with a segment of time within which the blood-pressure-pulse related event occurred in the pressure-affected body part, and determining the correction factor based on said segment of the reference data.

Optionally, air pressure higher than SBP value is applied over the pressure-affected body part before applying the monotonic decreasing pressure conditions thereon. The constant pressure higher than SBP value is applied for a predefined period of time sufficient to induce a condition causing increased blood flow in the pressure-affected body part after the pressure applied thereover is reduced below the SBP (as in reactive hyperemia conditions).

In some embodiments the changing pressure conditions are monotonically descending starting from a pressure level greater than a systolic blood pressure of the subject. In this case, the blood-pressure-pulse related event is an indication that the pressure applied over the pressure-affected body part became smaller than the systolic blood pressure of the examined subject. Alternatively the changing pressure conditions are monotonically ascending until reaching a pressure level greater than a systolic blood pressure of the subject, and wherein the blood-pressure-pulse related event is an indication that the pressure applied over the pressure-affected body part became greater than the systolic blood pressure of the examined subject.

In some embodiment the correction factor is determined by computing the ratio of the average value of a characteristic parameter of the blood-pressure-pulse related signal measured in the pressure-free body part within the time segment and the value of the characteristic parameter of a blood-pressure-pulse related signal measured in the pressure-free body part when the blood-pressure-pulse related event occurred in the pressure-affected body part.

The method may further comprise assessing sympathetic nervous activity of the examined subject by deriving a parameter (e.g., standard deviation of one or more of the characteristic parameters $I_D$, $I_S$ or $I_D$-$I_S$) that provides assessment of the variability of the blood-pressure-pulse related signals measured in a pressure-free body part.

BRIEF DESCRIPTION OF THE DRAWINGS

In order to understand the invention and to see how it may be carried out in practice, embodiments will now be described, by way of non-limiting example only, with reference to the accompanying drawings, in which like reference numerals are used to indicate corresponding parts, and in which:

FIG. 1B shows technique for the measurement of SBP, DSP and MBP by oscillometry, and FIG. 1C shows a curve of a PPG signal taken from a finger downstream an arm to which varying pressure conditions are applied by a cuff, and a curve of the cuff pressure as a function of time to demonstrate the reappearance of the PPG signals after cuff pressure decreases to below the SBP value;

FIGS. 3A to 3C demonstrate PPG signal variability, wherein FIG. 3A shows a typical PPG signal reflecting PPG variability, FIG. 3B shows the variability of the baseline ($I_D$ and $I_S$) values, and FIG. 3C shows the amplitude ($I_D$-$I_S$) variability;

FIGS. 11A and 11B exemplifies time window selection according to possible embodiments, where in FIG. 11A instantaneous absolute air pressure measurement and optical measurements are conducted in the pressure-affected body part and optical measurements are conducted in the pressure-free body part, and in FIG. 11B instantaneous absolute and oscillatory air pressure measurements are conducted in the pressure-affected body part and optical measurements are conducted in the pressure-free body part.

DETAILED DESCRIPTION OF EMBODIMENTS

Figure 1A:
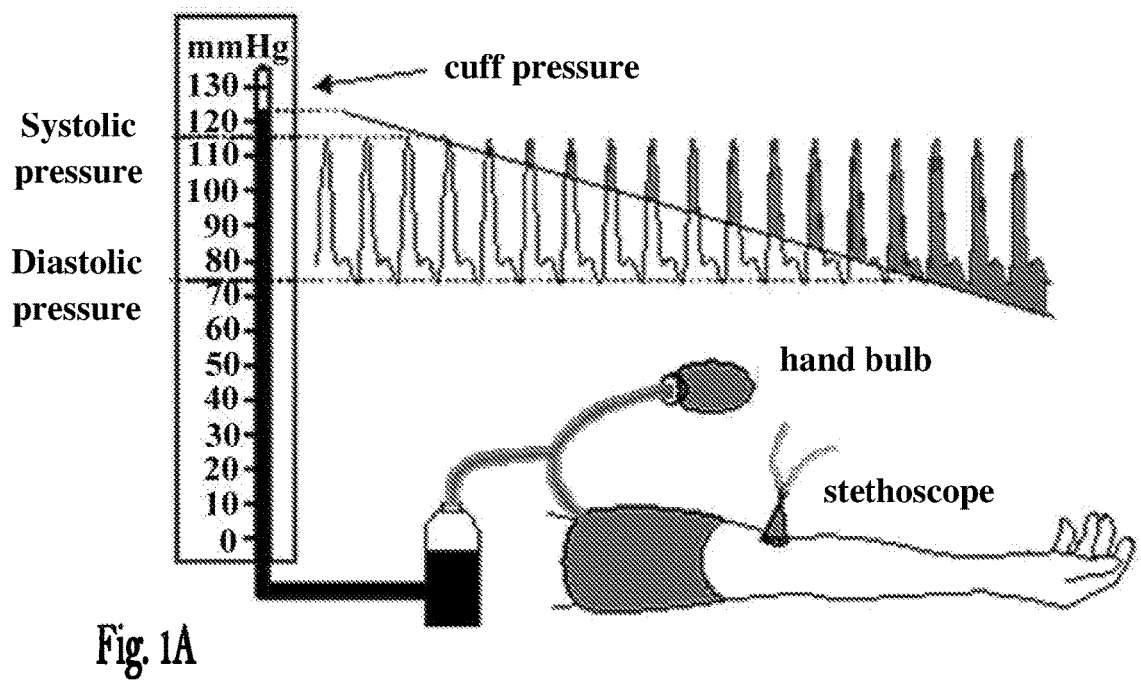
FIGS. 1A to 1C demonstrate available blood pressure measurement techniques, wherein FIG. 1A demonstrates a technique for measurement of SBP and/or DBP by Korotkoff-based manual sphygmomanometry.

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

The present disclosure provides in some of its embodiments improved techniques for measuring blood pressure parameters, SBP, DBP and/or MBP, in a subject. In the cuff-based blood pressure measurement techniques used nowadays (such as oscillometry and the Korotkoff sounds and the PPG based techniques) the SBP, DBP or MBP value is typically determined in a single blood pressure pulse, based on single acoustic/optical/air pressure pulse identification. Since the blood pressure parameters typically demonstrate spontaneous fluctuations, in particular respiratory-induced and very low frequency fluctuations of about 30-60 seconds time periods, the single blood pressure pulse measurement cannot faithfully represent the actual blood pressure parameters.

The accuracy of the SBP and DBP measurements obtained using the available cuff-based measurement methods is reduced due to the blood pressure changes occurring spontaneously from beat to beat (blood pressure variability). The blood pressure variability, which originates from several effects such as respiration and sympathetic activity, is associated with the PPG signal variability, and the fluctuations in the PPG parameters (such as signal minimum $I_D$, maximum $I_S$ and amplitude $I_D$-$I_S$) are correlated with the SBP and DBP fluctuations (Nitzan et al., 1999).

Similar to the other cuff-based SBP measurement techniques, in the PPG-based technique the SBP measurement is based on the identification of a PPG pulse that was the first to be detected/reappear during cuff deflation, which corresponds to a specific blood pressure pulse. In order to obtain more representative value of SBP, one may measure the SBP value for several pulses and use their average value.

One solution to the blood pressure variability problem is ambulatory blood pressure monitoring, in which repeated SBP measurements are conducted within consecutive cycles of inflation and deflation of the pressure cuff. However, each cuff inflation/deflation cycle used for each SBP measurement requires about 30 seconds and more, and these repeated cycles of cuff inflation and deflation are inconvenient. There is thus a need for more user-friendly blood pressure measurement techniques that will take account for the blood pressure variability.

Figure 1B:
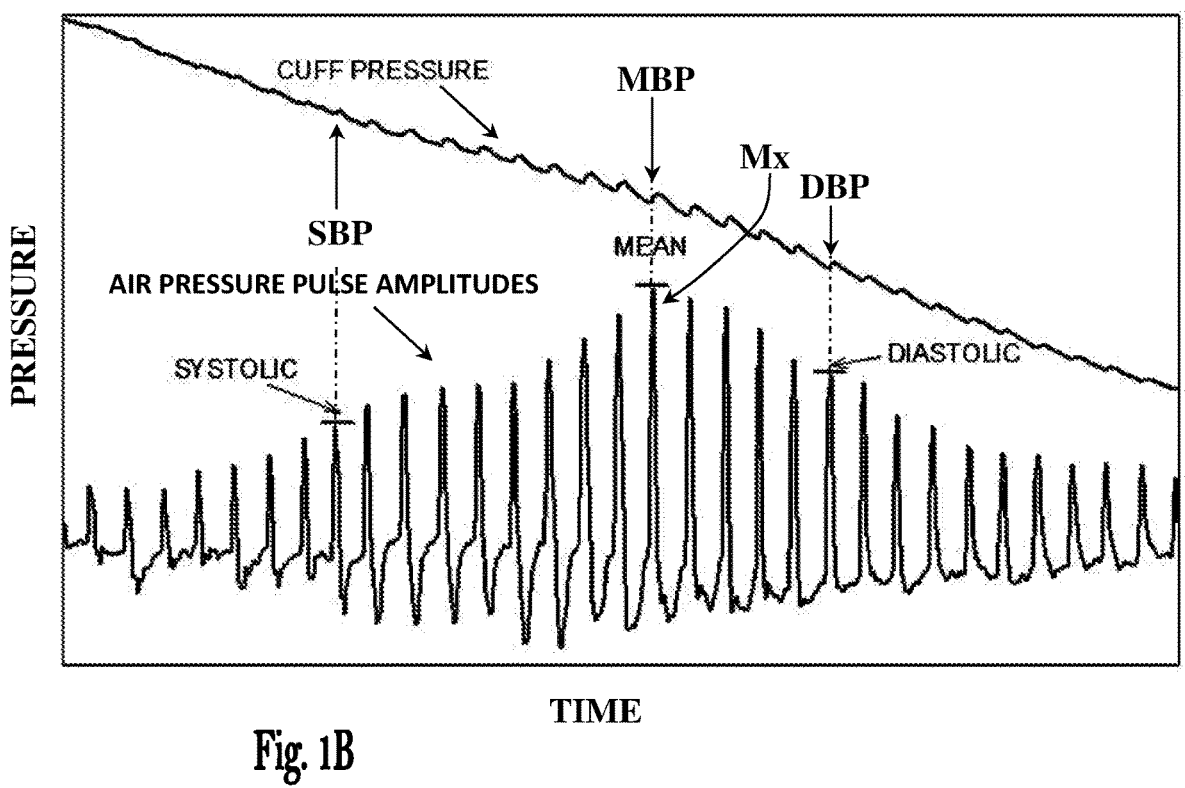

The blood pressure variability also affects the oscillometry technique wherein each of the blood pressure parameters, MBP, SBP and DBP, is measured based on a single corresponding blood pressure pulse having the required air-pressure pulse amplitude condition during the cuff deflation. Particularly, as demonstrated in FIG. 1B, the SBP and the DBP are derived in the oscillometry technique from the relationship between the air pressure pulse of maximal amplitude and corresponding other air pressure oscillations. The present invention provides techniques for assessment of the average value of the SBP, DBP and MBP of a subject. In some embodiments, parameters of blood-pressure-pulse related signals measured in a pressure-free body part of the subject are used to correct an initial blood pressure parameter value determined based on measurements simultaneously taken from a pressure-affected body part of the subject. In this way, the blood pressure variability reflected by the blood-pressure-pulse related signals measured in the pressure-free body part are used to correct the initial blood pressure parameters values measured in the pressure-affected body part, and thereby substantially increase the measurement accuracy.

It is a principal object of the present invention, in some of its embodiments, to evaluate the average SBP, DBP and/or MBP, of an examined subject from the initial SBP, DBP or MBP value, determined by identification of a blood-pressure pulse related event in measurement data obtained from the pressure-affected body part of the subject, by correcting the initial blood pressure parameter value according to the spontaneous blood pressure variability of the subject. For this purpose, in some embodiments, the spontaneous fluctuations of the measured blood-pressure-pulse related signals (e.g., PPG) measured in a pressure-free body part of the subject are used to determine a correction factor for adjusting the initial blood pressure value determined from the measurements obtained from the pressure-affected body part.

The correlation between the spontaneous fluctuations in the SBP, DBP or MBP of the examined subject and the corresponding fluctuations reflected in the blood-pressure-pulse related signals measured in the pressure-free body part, is advantageously employed in some embodiments to improve the accuracy of the SBP, DBP or MBP, determined based on the identification of the blood-pressure-pulse related event measured in the pressure-affected body part.

In some embodiments an initial SBP value of the examined subject is determined in a single blood pressure pulse (e.g., by detecting a PPG pulse or Korotkoff sounds or identifying a suitable air-pressure pulse, i.e. blood-pressure-pulse related changes, measured in a pressure-affected body part during application of descending/ascending air pressure conditions). Since the SBP shows spontaneous fluctuations (e.g., low frequency fluctuations typically occurring within 30-60 seconds time periods), the average SBP of the subject is evaluated by adjusting the initial SBP value determined from the single pulse SBP measurement by means of the spontaneous fluctuations of blood-pressure-pulse related signals measured in a pressure-free body part of the subject, utilizing the correlation between the spontaneous fluctuations in the SBP of the examined subject and characteristic parameters of the blood-pressure-pulse related signals from the pressure-free body part to correct the initial SBP value.

In some embodiments, a PPG sensor is used to generate optical data measured in the pressure-affected body part during application of descending air pressure conditions, and the reappearance of the PPG pulses, and/or the start of declination of the light transmission curve, once the pressure applied over the pressure-affected body part is reduced below the SBP value, is used to determine the initial SBP value of the subject.

In some embodiments, the time term during which the cuff pressure is raised to above SBP value is prolonged to about 50 to 100 seconds and in some embodiments up to 300 seconds in order to induce in the pressure-affected body part a state resembling reactive hyperemia conditions, to thereby cause an increase in blood volume during systole after the applied pressure in reduced below the SBP value. The increased blood flow results in an increase of the PPG pulsating component measured in the pressure-affected body part when the applied pressure is slightly below the SBP of the examined subject.

Figure 6A:
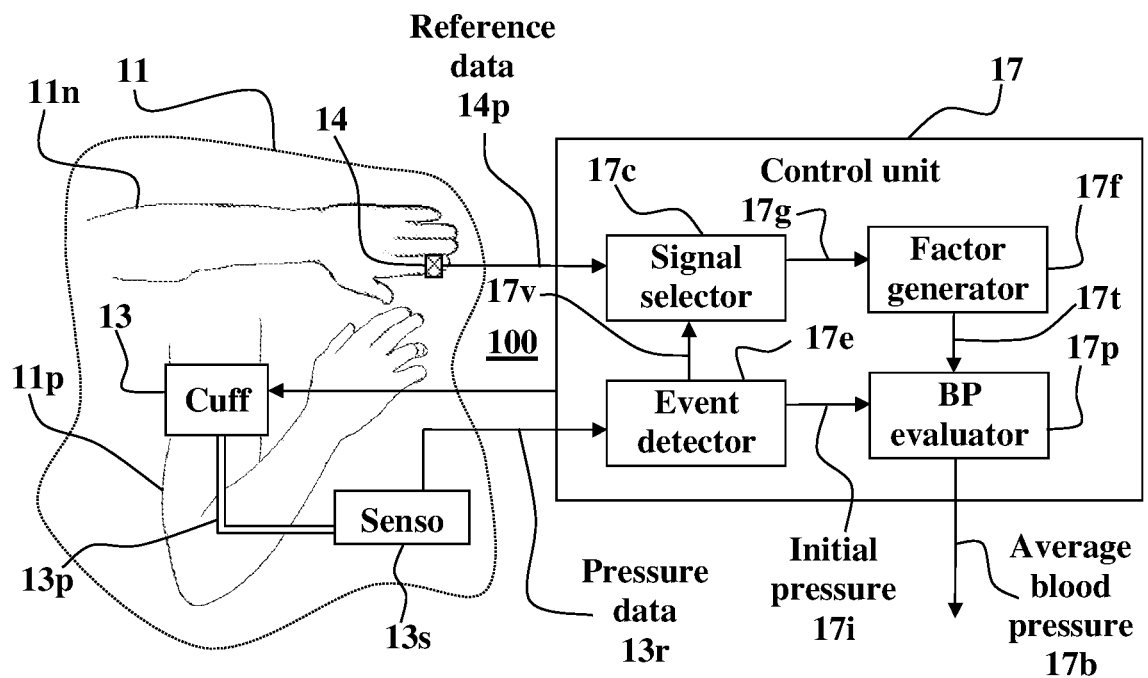
FIGS. 6A and 6B schematically illustrate systems for evaluating blood pressure of a subject according to some possible embodiments, where in the system of FIG. 6A only instantaneous absolute and oscillatory air pressure measurements are taken from the pressure-affected body part/limb, and in the system of FIG. 6B an additional probe is used to conduct optical or acoustic measurements in the affected body part/limb.

With reference to FIG. 6A, in some embodiments, a pressure device 13, comprising a pressure pump and a pressure applying element (also referred to herein as pressure element e.g., cuff device), is used for applying ascending or descending pressure conditions over a region of an organ/body part 11$p$ (e.g., an arm of a limb) of an examined subject 11. A pressure sensor 13$s$ is used to measure the pressure applied over the pressure-affected body part and generate pressure data 13$r$ indicative thereof. In this non-limiting example the pipe 13$p$ is used to communicate the cuff pressure to the pressure sensor 13$s$, however, in possible embodiments the pressure sensor 13$s$ may reside in any location in the pressure device, or the pressure cuff, that is suitable for sensing the pressure applied over the body part 11$p$.

The system 100 comprises a reference measuring unit 14 (e.g., using a pressure or optical probe) configured to measure blood-pressure-pulse related signals in a pressure-free body part 11$n$, and generate reference data 14$p$ indicative thereof. The control unit 17 is configured to operate the pressure device 13 to apply the pressure conditions over the pressure-affected body part 11$p$, and process the pressure data 13$r$ and the reference data 14$p$ for determining the required average blood pressure parameter 17$b$ of the examined subject 11.

The control unit 17 comprises an event detector 17$e$, a signal selector unit 17$c$, a factor-calculating unit 17$f$, and a blood pressure evaluator 17$p$. The event detector 17$e$ is configured and operable to process and analyze an oscillatory component of the (air) pressure data 13$r$, identify therein a certain blood-pressure related event, and accordingly issue a respective event indication 17$v$ (also referred to herein as time indication) and determine the initial blood pressure parameter 17$i$ of the examined subject 11 accordingly, utilizing the instantaneous absolute pressure data 13$r$. The signal selector 17$c$ is configured and operable to process the reference data 14$p$ and select therein a group of consecutive blood-pressure-pulse related signals 17$g$ (measured within a predefined time/signal window), based on the event indication 17$v$ issued by the event detector 17$e$. The factor-calculating generator 17$f$ is configured and operable to process the group of consecutive pulse signals 17$g$ selected by the chopper-selector 17$c$ and determine therefrom a correction factor 17$t$ for the determination of the average blood pressure parameter of the examined subject 11. The blood pressure evaluator 17$p$ is configured and operable to correct the initial blood pressure 17$i$ determined by the event detector 17$e$ with the correction factor 17$t$ from the factor-calculating generator 17$f$ to determine an average blood pressure parameter 17$b$ of the examined subject 11.

Figure 6B:
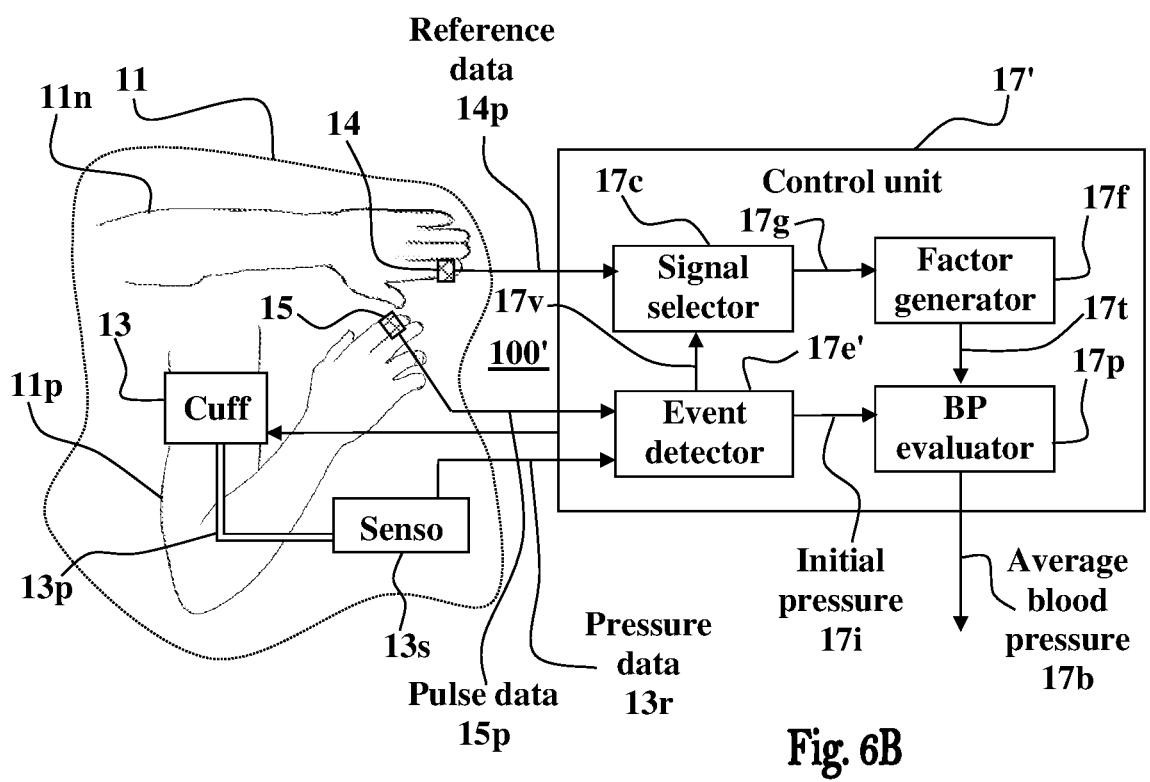

FIG. 6B shows a system 100' in which an additional measuring unit 15 (e.g., optical or acoustic probe) is used for measuring blood-pressure-pulse related signals 15$p$ in the pressure-affected body part 11$p$. The system 100' is substantially similar to the system 100 shown in FIG. 6A, where the main difference between these systems being the operation of the event detector 17$e$' of the control unit 17' of system 100'. Particularly, the event detector 17$e$' of the system 100' is configured and operable to process the pulse data 15$p$ from the additional measuring unit 15 and identify therein a certain blood-pressure-pulse related event associated with pressure conditions applied by the pressure device 13 (re-appearance/vanishing of blood-pressure-pulse related signals,). Upon identifying the certain blood-pressure-pulse related event, the event detector 17$e$' issues the event indication 17$v$ and determined from the pressure data 13$r$ the initial blood pressure value 17$i$ as the pressure applied by the pressure device 13 at the time the certain event occurred. The chopper/selector 17$c$, factor-calculating generator 17$f$ and the evaluator 17$p$, perform substantially the same operations as described hereinabove with reference to FIG. 6A.

In some embodiments a PPG probe is used in the additional measuring unit 15 to measure transmission of light through an examined tissue in the pressure-affected body part 11$p$ (distal/downstream to the pressure element) and generate optical data 15$p$ indicative thereof, and another PPG probe is used in the reference measuring device 14 to measure transmission of light through an examined tissue in the pressure-free body part 11$n$ and generate optical data indicative thereof. The control unit 17' is used to simultaneously operate the pressure device 13 and the PPG probes, process the pressure data 13$r$ from the pressure device 13 and the optical data, 15$p$ and 14$p$, from the PPG probes, and determine one or more average blood pressure parameters 17$b$ (e.g., SBP) of the examined subject based thereon.

The PPG probes are configured in some embodiments to optically couple to respective tissue regions in the pressure-affected body part, distal (i.e., downstream) to the pressure element, and in the pressure-free body part, illuminate the examined tissue regions with light measure the light transmitted or reflected through/from the examined tissue, and generate optical data indicative thereof. The control unit is configured in some embodiments to activate the pressure device to increase the pressure applied over the pressure-affected body part to a pressure greater than the SBP and then to gradually release the pressure applied thereover, while simultaneously activating the PPG probes to illuminate the examined tissue regions and provide responsive optical data.

The present disclosure also provides an improved technique of increasing the amplitude of the PPG pulses obtained from the tissue downstream the pressure-affected region of the pressure-affected body part at cuff pressures slightly below the SBP. For this purpose, in some possible embodiments, the pressure cuff is inflated to exert pressure above the SBP and maintain the above SBP pressure level for about 60 seconds, or more, in order to induce occlusive conditions resembling reactive hyperemia conditions, which result in increase of the PPG pulses, and steeper decrease of the DC component. The cuff pressure is then gradually reduced, and the blood-pressure-pulse related signals are measured in the pressure affected body part 11$p$ and the pressure-free body part 11$n$. In this case the AC and DC components of the blood-pressure-pulse related signals measured at cuff pressures slightly below the SBP in the pressure affected body part 11$p$ present improved SNR due to the prolonged occlusive conditions applied over the pressure-affected body part.

Figure 8:
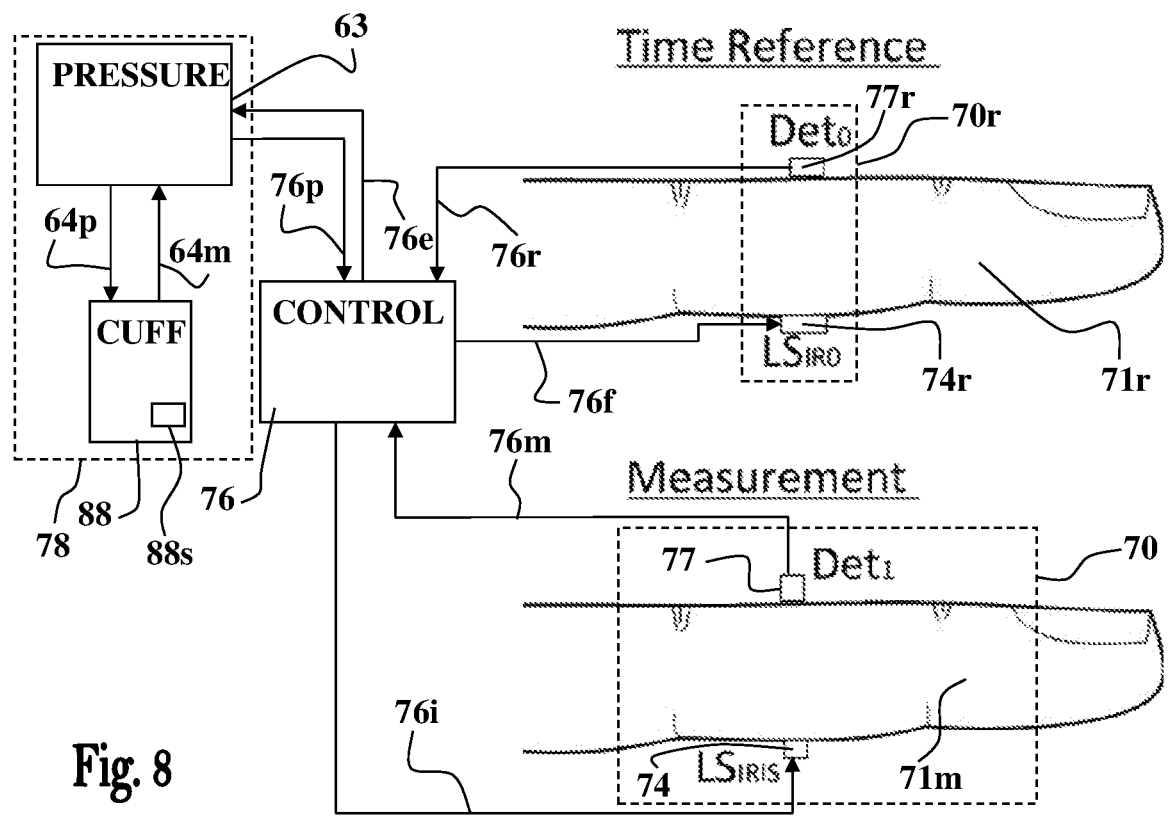
FIG. 8 schematically illustrates a PPG probe designed to measure PPG signals from fingers of a subject according to some possible embodiments.
Figure 9:
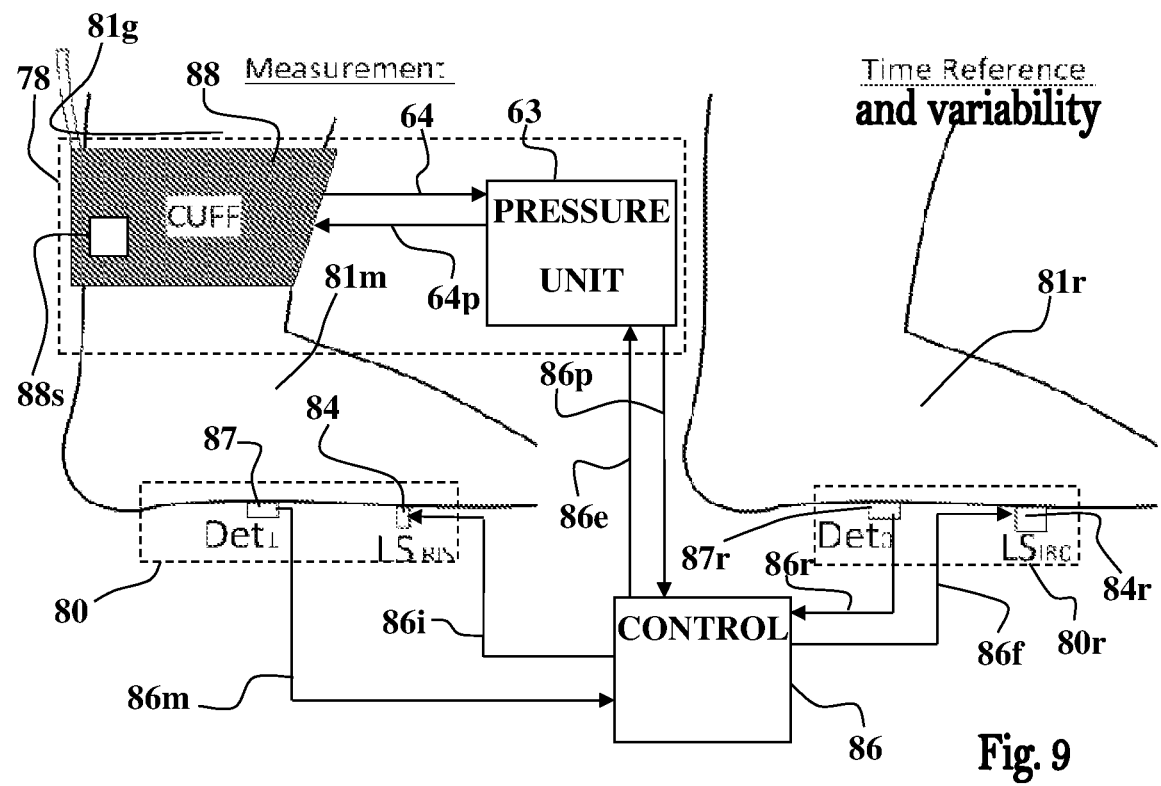
FIG. 9 schematically illustrates a PPG probe designed to measure PPG signals from feet of a subject according to some possible embodiments.

FIG. 8 and FIG. 9 demonstrate PPG probes, 70 and 80, of the measuring unit 15 configured according to some possible embodiments for measuring PPG signals in a finger 71$m$ of a pressure-affected arm of a subject, and in the foot 81$m$ of a pressure-affected leg of a subject (e.g., a neonate), respectively. Reference PPG probes, 70$r$ and 80$r$ respectively, of the reference measuring unit 14 are configured in possible embodiments to measure time reference PPG signals from organs/body parts which are not subject to the applied pressure conditions (71r and 81r respectively i.e., pressure/cuff-free organ). For example, in possible embodiments the reference PPG probe 70r/80r may include an infrared light source ($LS_{IR0}$) 74r/84r and a light detector ($Det_0$) 77r/87r, configured to measure the time reference PPG signal from a finger 71r/foot 81r in the contralateral hand/leg of the examined subject in a transmission/reflection-mode configuration. These PPG signals in the pressure-free hand/foot are used for determining a correction factor for the initial blood pressure parameters, and may also be utilized as time reference to improve the reliability of the detection of the reappearance of the PPG pulses in the PPG signals measured in the examined tissue regions of finger 71m and of foot 81m.

In some embodiments, the time-reference PPG signals are used to assist in differentiating between the faint PPG pulses reappearing once the pressure applied over the pressure-affected body part decrease below the SBP and changes in the light transmission curve due to background noise. Alternatively, or additionally, the pressure pulses in the pressure cuff (and/or ECG R-wave signals from an external ECG device) may also be used as a time-reference to assist in differentiating between the weak reappearing PPG pulses from changes due to the background noise.

Figure 1C:
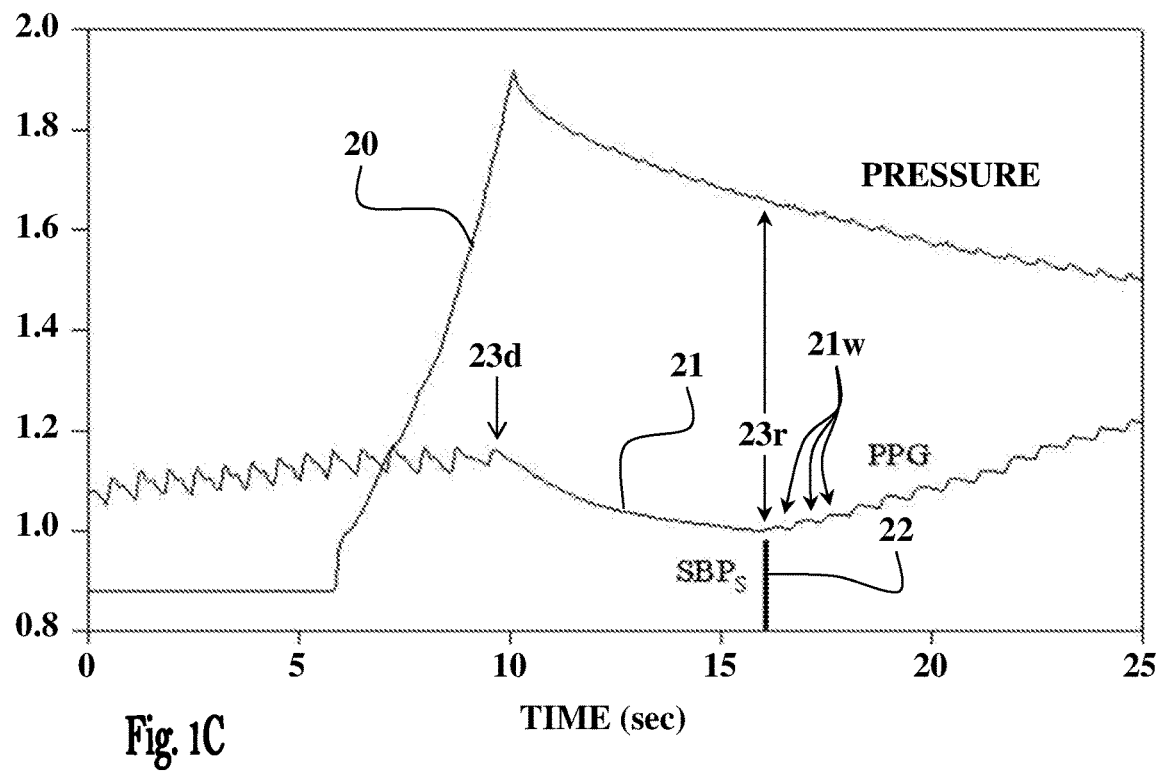
Figure 2:
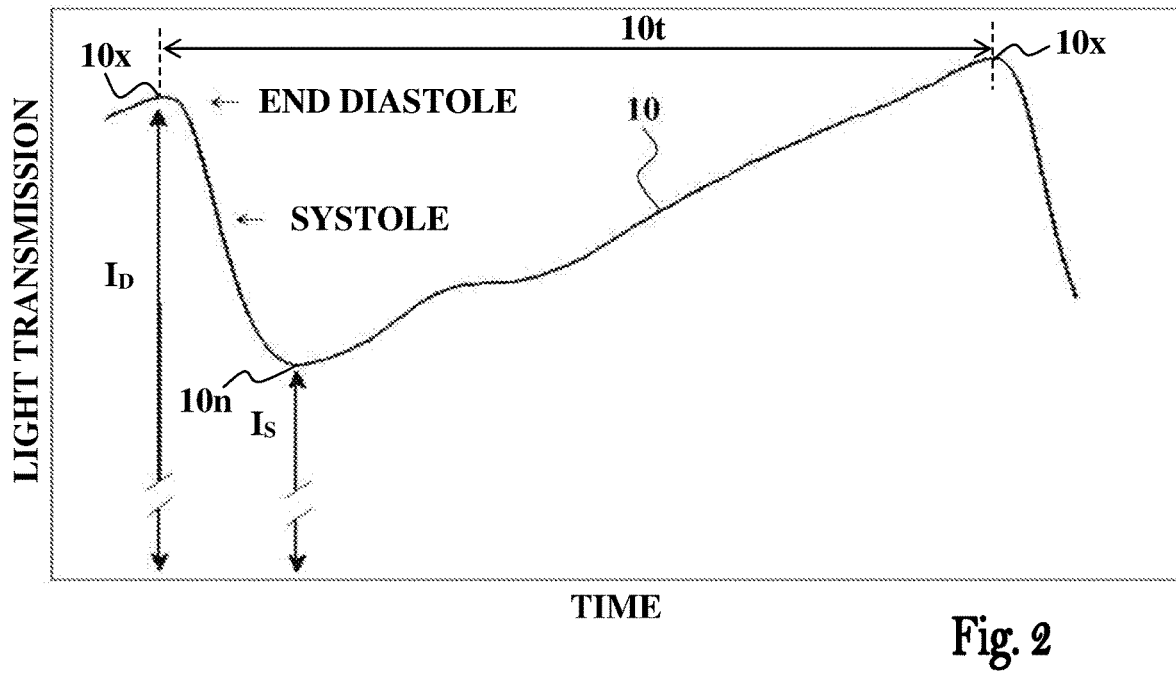
FIG. 2 shows a single PPG pulse signal.
Figure 3A:
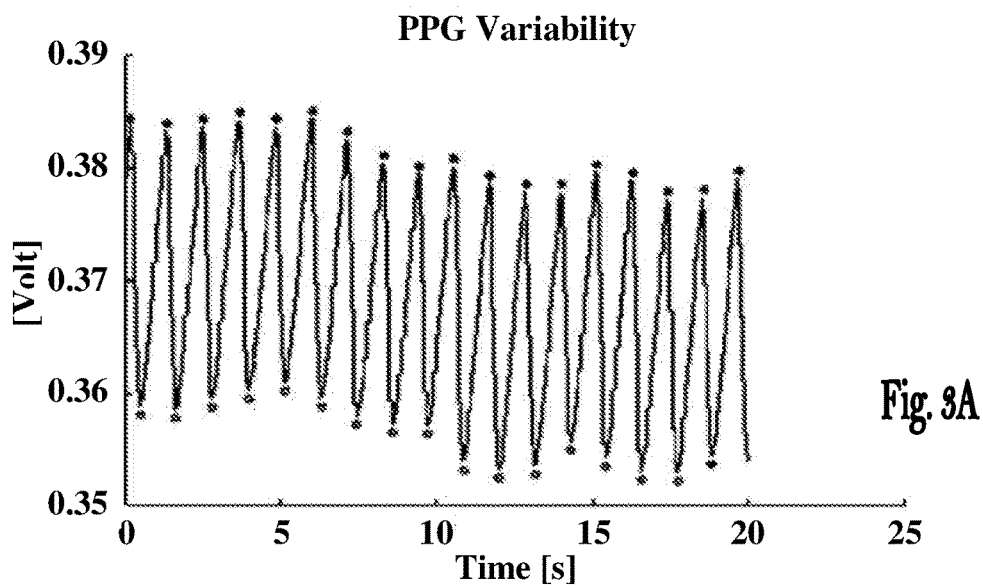
Figure 3B:
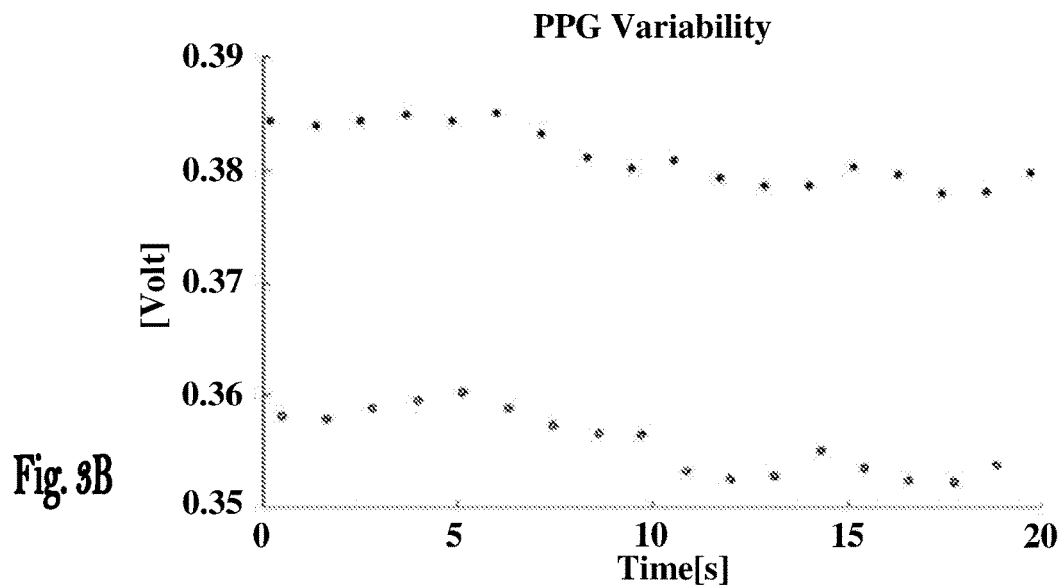
Figure 3C:
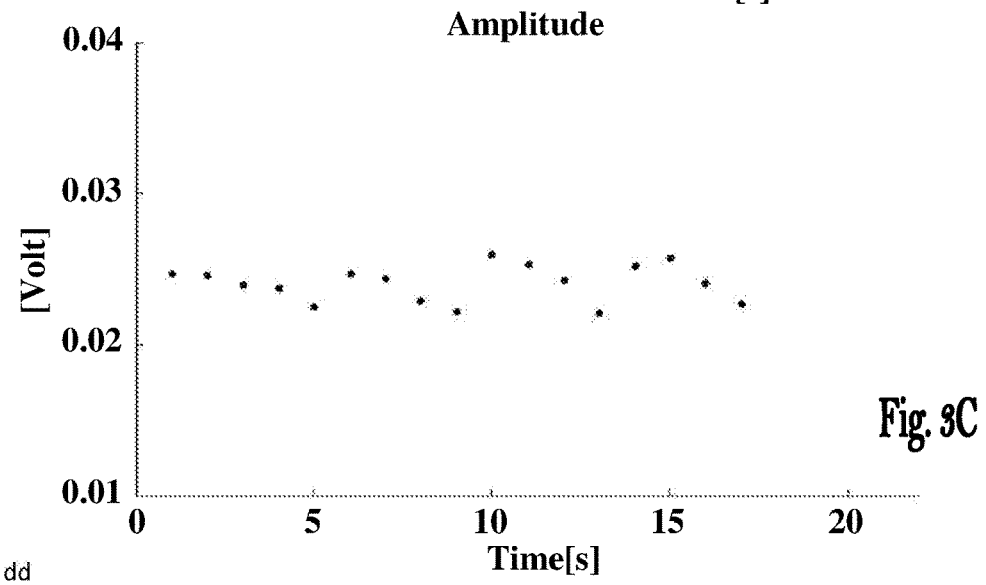

With reference to FIG. 8, a control unit 76 may be used to operate the PPG probe 70 of the measuring unit and a pressure applying device 78. The pressure applying device 78 comprises a pressure cuff 88 placed over the arm (not shown) of the examined subject and a pressure unit 63 comprising a pressure pump configured to operate the cuff 88 to apply pressure over the arteries of an arm upstream to the finger 71m, and a pressure measuring transducer 88s adapted to measure the air pressure in the cuff 88. In this example the control unit 76 is configured to operate the $LS_{IRIS}$ light source 74 by generating respective control signals 76i, and receive respective measured light intensity signals 76m (also referred to herein as optical data) from the light detector $Det_1$ 77. The control unit 76 may be configured to activate the pressure unit 63 to apply varying pressure conditions (e.g., as exemplified by curve 20 in FIG. 1C) by the pressure cuff 88 over the arm of the examined subject by producing respective control signals 76e, and to receive measured pressure data 76p from the pressure measuring transducer 88s in the pressure unit 63 indicative of the pressure applied over the pressure-affected arm.

The control unit 76 is configured to implement an event detector (17e' in FIG. 6B) that process and analyze the measured optical data 76m and identify in it a blood-pressure-pulse related event associated with the varying pressure conditions applied by the pressure cuff 88, and determine the amount of pressure the pressure cuff 88 applies at the time the blood-pressure-pulse related event occurred in the finger 71m. The pressure applied by the pressure cuff 88 at the time the blood-pressure-pulse related event occurred is defined as an initial blood pressure (17i e.g., SBP or DBP) value of the examined subject.

The control unit 76 is further configured to simultaneously operate the reference PPG probe 70r of the measuring unit and obtain therefrom reference optical data for determining a respective correction factor. More particularly, the control unit 76 may be configured to operate the $LS_{IR0}$ 74r light source simultaneously during the same time periods in which the varying pressure conditions are applied by the pressure device 78, by producing corresponding control signals 76f to illuminate the pressure-free finger 71r in the contralateral hand (or another pressure free limb or organ) of the subject, and receive corresponding measured light transmission signals 76r (also referred to herein as reference optical data) from the detector $Det_0$ 77r.

The control units 76 can be configured substantially similar to control unit 17' shown in FIG. 6B. Referring now to FIG. 11A, the control unit 76 is configured to implement a signal selector (17c in FIGS. 6A and 6B) that process the reference optical data 76r and identify therein a PPG pulse measured in the contralateral pressure-free hand at the same time the blood-pressure-pulse related event 23r occurred in the pressure-affected hand (SBP in this example identified by the reappearance of the PPG signals). The control unit 76 then derives at least one PPG property (also referred to herein as a PPG characteristic parameter, such as the point of minimum, point of maximum (baseline) and amplitude, of the PPG pulse) of PPG pulses in a selected group/window 55 of consecutive PPG pulses in the measured reference optical data 76r. The group/window 55 of consecutive PPG signals includes, and centered about, the PPG pulse measured in the contralateral hand at the time the blood-pressure pulse related event occurred in the pressure-affected hand.

More particularly, the control unit 76 identifies in the reference optical data 76r a PPG pulse 53 occurred in the pressure-free contralateral hand at the time the blood-pressure-pulse related event occurred in the pressure-affected hand, and then defines a time/signal window 55, including 2N+1 consecutive PPG pulses and centered about the PPG pulse 53. In some embodiments, the control unit 76 implement a factor-calculating generator (17f in FIGS. 6A and 6B) that processes and analyzes PPG pulses in the predefined time/signal window 55 defined in the measured reference optical data 76r comprising 2N+1 PPG pulses centered about the PPG pulse 53 measured in the contralateral hand at the time the blood-pressure-pulse related event 23r occurred in the pressure-affected hand. The control unit 76 then calculates the average of one of the derived PPG parameters over the 2N+1 PPG pulses in the time window 55, and utilizes the calculated average value to compute a correction factor (17t) for assessing the average blood pressure parameter (17b e.g., SBP or DBP) of the examined subject.

In preferred embodiments the correction factor (17t) is an average-to-single pulse ratio between the calculated average PPG characteristic parameter value and the PPG characteristic parameter value determined for the PPG pulse 53 measured in the contralateral hand at the time the blood-pressure-pulse related event occurred in the pressure-affected hand. The average blood pressure parameter (e.g., SBP or DBP) of the examined subject is then determined by multiplying the correction factor (17t) by the initial blood pressure (17i e.g., SBP or DBP) value of the examined subject. For example, and without being limited, if the maximum values $MX_1$, $Mx_2$, $MX_3$, . . . of the PPG signals are used as the PPG characteristic parameters, then the control unit 76 calculates the average of the maximum values $A_{vrg}=\Sigma_1^{2N+1} MX_i/(2N+1)$. The computed average $A_{vrg}$ and the PPG characteristic parameter $MX_{N+1}$ of the PPG pulse 53 about which the time window 55 is centered are then used to determine the correction factor (17t) as the average-to-single-pulse ratio $CF=A_{vrg}/MX_{N+1}$. Similarly, the correction factor CF (17t) can be calculated using the minimum value of the PPG pulse signals as the PPG characteristic parameter, or the amplitude values of the PPG pulses as the PPG characteristic parameter.

In the example of FIG. 11A instantaneous absolute air pressure measurement 76p and optical measurements 76m (and/or acoustic and/or tonometry) are conducted in the pressure-affected body part and optical measurements 76r (and/or acoustic and/or tonometry) are conducted in the pressure-free body part. FIG. 11B schematically illustrates determining an average blood pressure parameter value of an examined subject using the system 100 of FIG. 6A, in which the air pressure sensor 13s is configured to measure both instantaneous absolute air pressure and oscillometric air pressure pulses indicative of blood-pressure-pulse related signals 76m' in the pressure-affected body part, and the reference measurement unit 14 comprises a PPG sensor (and/or air pressure and/or tonometry sensor) configured to measure blood-pressure-pulse related signals 76r in the pressure-free body part. In this configuration the event detector 17e is configured and operable to identify the blood-pressure-pulse related event 23r as the occurrence of an air pressure pulse signal 53' of maximal amplitude in the pressure-affected body part.

The event detector 17e is configured and operable to identify in the air pressure pulse signals 76m' measured in the pressure-affected body part an air pressure pulse 53' of maximal amplitude for determining an initial MBP value for the examined subject The event detector 17e then identifies an air pressure pulse 54 based on the initial MBP value (e.g., 60% of the MBP value) and a point in time (17v) at which the air pressure pulse signal 54 occurred. The signal selector 17c then identifies in the reference optical data 76r a blood-pressure-pulse related signal 54' measured in the pressure-free body part at the time at which the SBP air pressure pulse signal 54 been measured in the pressure affected body part. The signal selector 17c then defines a time window 55, including 2N+1 consecutive PPG pulses centered about the PPG pulse 54' measured in the pressure-free body part at the time of the SBP pressure pulse signal 54, and process the PPG pulses within the time window 55 to compute a correction factor 17t for determining the average SBP 17b based on the initial SBP value 17i, as described hereinabove.

The computation scheme illustrated in FIG. 11B may be similarly used to determine an initial DBP value from the air-pressure pulse signals 76m' for identifying the DBP related air-pressure pulse signal 56 and the corresponding blood-pressure-pulse related signal measured in the pressure-free body part at the time at which the DBP related pressure pulse signal 56 was measured. A correction factor 17t for determining the average DBP 17b of the subject can be then determined by defining a time window centered about the blood-pressure-pulse related signals measured in the pressure-free body part at the time at which the DBP-related pressure pulse signal 56 was measured, as described hereinabove.

In some embodiments, the average blood pressure computation scheme illustrated in FIGS. 11A and 11B is similarly carried out, mutatis mutandis, using in the measuring unit 15 an acoustic signal sensor configured and operable for detecting Korotkoff sounds in the pressure-affected body part. Mutatis mutandis, the average blood pressure computation scheme illustrated in FIGS. 11A and 11B is carried out in some embodiments using in the reference measuring unit 14 oscillometric/pressure sensor configured to measure blood-pressure-pulse related signals in the pressure-free body part. Similarly, in some embodiments, the average blood pressure computation scheme illustrated in FIGS. 11A and 11B is carried out, mutatis mutandis, using in the additional measuring unit 15 an acoustic signal sensor configured and operable for detecting Korotkoff sounds in the body part and using in the reference measuring unit 14 oscillometric/pressure sensor for measuring heart-induced pulse signals in the pressure-free body part of the subject.

Referring now to FIG. 9, the control unit 86 is also configured and operable to implement the function blocks of the control unit 17' shown in FIG. 6A, as will be explained hereinbelow. The control unit 86 is configured to operate the PPG probe 80 and the pressure device 78, comprising the pressure cuff 88 placed over the neonate leg 81g and configured to apply pressure over the arteries upstream to the foot 81m. In this non-limiting example the control unit 86 is configured and operable to operate the $LS_{IRIS}$ light source 84 by generating respective control signals 86i, and receive respective measured light intensity reflection signals 86m from the detector $Det_1$ 87. The control unit 86 may be configured to activate the pressure pump in the pressure device 78 to apply varying pressure conditions (e.g., as exemplified in FIG. 1C) by the pressure cuff 88 over the ankle 81g of the neonate by producing respective control signals 86e, and to receive measured pressure data 86p from the pressure measuring transducer 88s in the pressure device 78 indicative of the pressure applied over the ankle 81g.

It is noted that the transducer 88s can be situated in, or under the pressure cuff 88, or external to the cuff 88 (e.g., in the pressure unit 63, or elsewhere) and in pressure communication with the pressure cuff by means of a pipe, as exemplified in FIGS. 6A and 6B.

In a similar manner, the control unit 86 is configured and operable to process and analyze the measured optical data 86m and identify in it a blood-pressure-pulse related event associated with the varying pressure conditions applied by the pressure cuff 88 and determine the amount of pressure the pressure cuff 88 applies at the time the blood-pressure-pulse related event occurred. The pressure applied by the pressure cuff 88 at the time the blood-pressure-pulse related event occurred in the pressure-affected body part is defined as an initial SBP value (17i) of the examined subject.

The control unit 86 is further configured to simultaneously operate the reference PPG probe 80r for simultaneously measuring blood-pressure-pulse related signals in the pressure-free body part 81r for computing the correction factor (17t) for the determined initial blood pressure value of the subject. More particularly, the control unit 86 operates the $LS_{IR0}$ 84r light source during the same time periods in which the varying pressure conditions are applied by the pressure device 78 by producing corresponding control signals 86f to illuminate the contralateral pressure-free foot 81r (or another pressure free limb or organ of the neonate) and receiving corresponding measured light transmission signals 86r (reference optical data) from the detector $Det_0$ 87r. The measured reference optical data 86r is then used by the control unit 86 to compute a correction factor (17t) for determining the average SBP (17b) of the examined subject, as described hereinabove.

In some embodiment the average blood pressure value 17b is determined with the configuration illustrated in FIG. 9 using an optical measurement sensor (e.g., PPG sensor), a pressure sensor (e.g., tonometer sensor), and/or an acoustic signal sensor (e.g., microphone), for measuring the blood-pressure-pulse related signals in the pressure-affected body part i.e., in the foot 81m. Similarly, in some embodiments, the average blood pressure value is determined with the configuration illustrated in FIG. 9 using in the reference measuring unit, an optical measurement sensor (e.g., PPG sensor) or a pressure sensor (e.g., tonometer), for measuring the heart-induced pulse signals in the pressure-free body part i.e., in the foot 81r.

Figure 7:
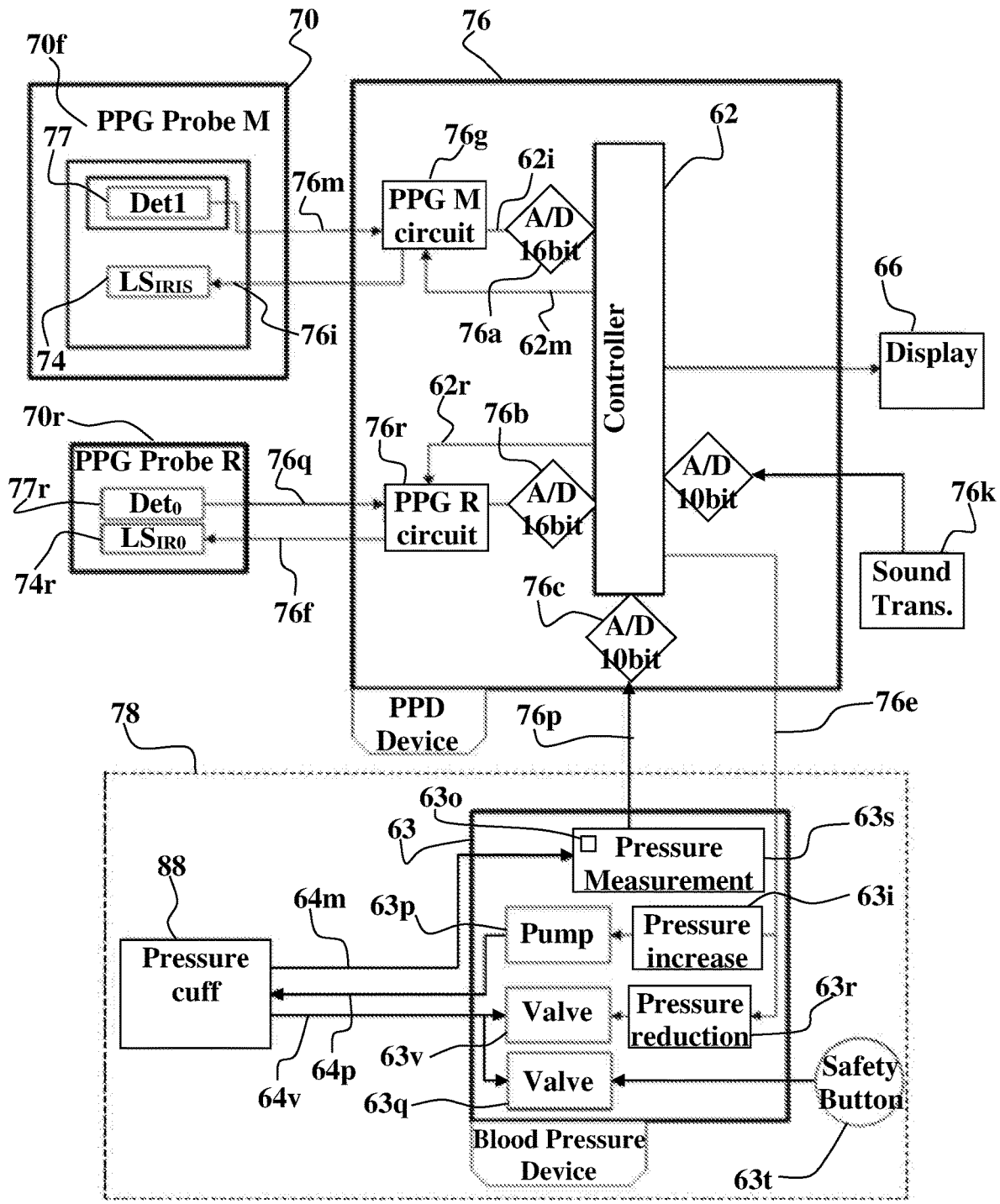
FIG. 7 is a block diagram of a PPG-based blood pressure measurement device according to some possible embodiments.

FIG. 7 is a block diagram illustrating a system using the control unit 76 for determining an average blood pressure value of a subject using a PPG probe in the measuring unit 70 for measuring PPG signals from the examined tissue in the pressure-affected body part, and the pressure device 78 for applying ascending/descending pressure conditions to an organ/body part upstream to the examined tissue. The control unit 76 in this example comprises a controller 62 and a PPG signal measurement unit 76g configured to operate the PPG sensor of the measurement unit 70 responsive to control signals 62m received from the controller 62.

For example, the PPG signal measurement unit 76g may be configured and operable to issue control signals 76i, to activate the light source $LS_{IRIS}$ 74, responsive to one or more control signals 62m from the controller 62, and optionally amplify and/or filter (if so needed), respective light transmission/refraction intensity signals 76m received from the detector $Det_1$ 77 responsive to light from the light sources 74. The PPG signal measurement unit 76g is further configured to transfer the received light intensity signals 76m to a sampling unit 76a (A/D) configured to digitize the light intensity signals 76m and to provide the resulting digital data to the controller 62.

The controller 62 in this example is further configured to issue pressure control signals 76e for activating the pressure unit 63 of the pressure device 78, and a sampler unit 76c configures to digitize pressure signals 76p indicative of the pressure applied by the pressure cuff 88 over the organ and provide the resulting digitized data to the controller 62. More particularly, in some embodiments the pressure device 78 may comprise a pressure cuff 88 coupled to the pressure unit 63 via a pressure injection line 64p configured to communicate pressure between the pump 63p and the cuff 88 in the pressure unit 63 to inflate the cuff 88, and a pressure discharge line 64v configured to discharge pressure from the cuff 88 through a controlled valve 63v and a safety valve 63q provided in the pressure unit 63 to discharge pressures from the cuff 88.

The pressure unit 63 may further comprise a pressure increasing unit 63i configured to operate the pump 63p responsive to control signals 76e from the controller 62 instructing the pressure unit 63 to increase the pressure in the cuff 88, and a pressure reducing unit 63r configured to operate the controlled valve 63v to discharge pressure from the cuff 88 responsive to control signals 76e from the controller 62 instructing the pressure unit 63 to reduce the pressure in the cuff. The pressure cuff 88 is connected by a tube 64m to a pressure measurement unit 63s provided in the pressure unit 78 and comprising a pressure sensor 63o. The pressure measurement unit 63s is configured to generate pressure measurement signals 76p, optionally amplify and/or filter (if so needed) the pressure measurement signals 76p, and provide the pressure signals 76p to the control unit 76 over a pressure measurement line. The safety valve 63q in some embodiments may be a normally-closed pressure valve configured to discharge cuff pressure by manual activation of a safety button 63t by a user, to thereby permit the user to change the state of the safety valve 63q into an open state, if so needed.

In some possible embodiments the control unit 76 is configured and operable to maintain the maximal (greater than SBP) air pressure applied over the pressure-affected body part for time periods between 1 to 5 minutes in order to occlude the arteries under the cuff and to induce a condition resembling reactive hyperemia conditions therein.

The control unit 76 may further comprise in some embodiments a display device 66 on which processed data from the controller 62, such as determined systolic blood pressure and heart rate. Additionally or alternatively, the control unit 76 may comprise a USB controller configured to exchange data with an external computer system.

In some embodiments the control unit 76 may further include a PPG reference signal measurement unit 76r, configured to operate the additional PPG probe of the reference measuring unit 70r coupled to a pressure-free organ responsive to control signals 62r received from the controller 62. More particularly, the PPG reference signal measurement unit 76r may be configured to issue the control signal 76f to activate the $LS_{IRO}$ light source 74r of the additional PPG probe of the reference measuring unit 70r responsive to control signal 62r from the controller 62, receive, and optionally amplify and/or filter (if so needed), light transmission intensity signals 76q from the detector $Det_0$ 77r and transfer the same to a sampling unit 76b configured to digitize the received light intensity signal and provide the resulting digital data to the controller 62.

The controller 62 may comprise a processor and memory devices for storing programs and other data for operating the units 76, 70, 70r, and 78 of the system. For example, the controller 62 may be configured to operate the PPG probe of the measuring unit 70 (and optionally also the reference PPG probe of the measuring unit 70r) and the pressure device 78, process the optical and pressure data responsively received, and determine the average systolic pressure of the examined subject using one or more of the methods described hereinabove or hereinbelow.

Figure 4:
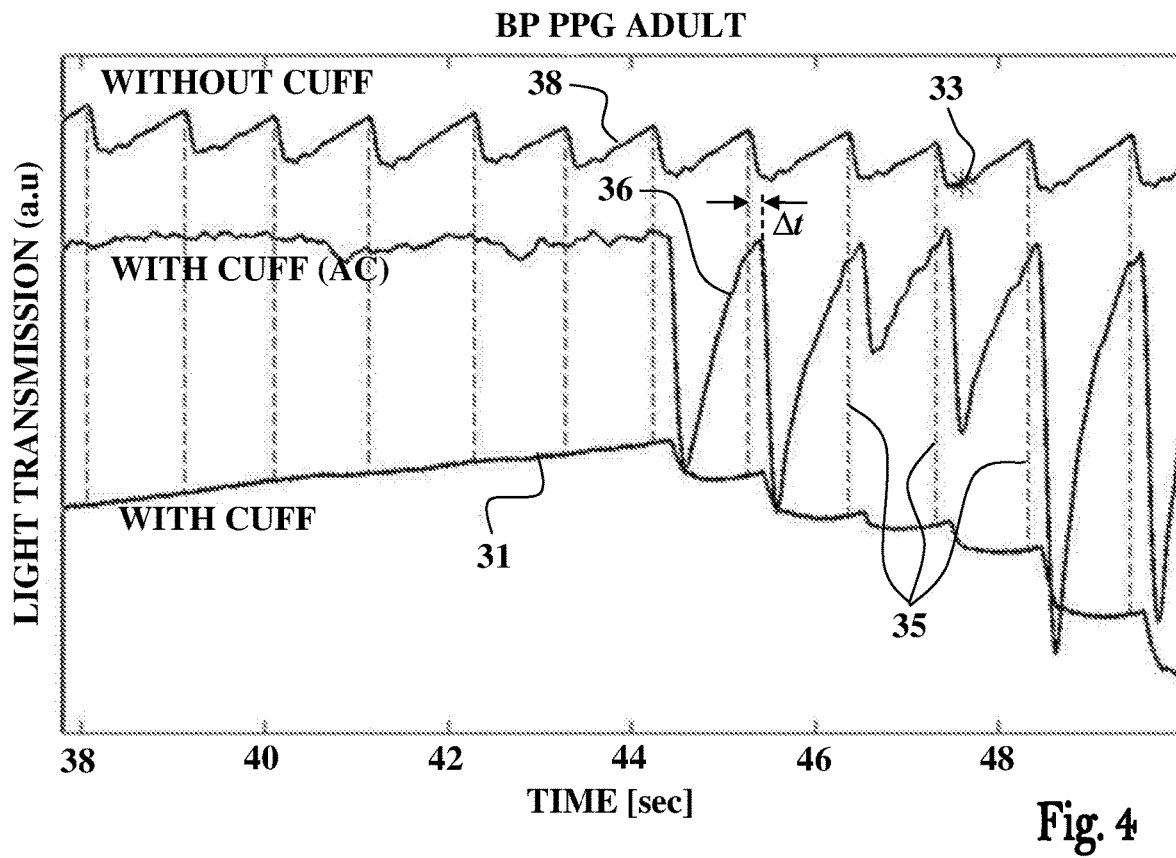
FIG. 4 shows raw light transmission and AC PPG signal curves taken from a finger in one hand of an adult subject during the deflation of a cuff situated over the corresponding arm and a cuff-free PPG signal simultaneously taken from a finger in the other hand of the subject.
Figure 5:
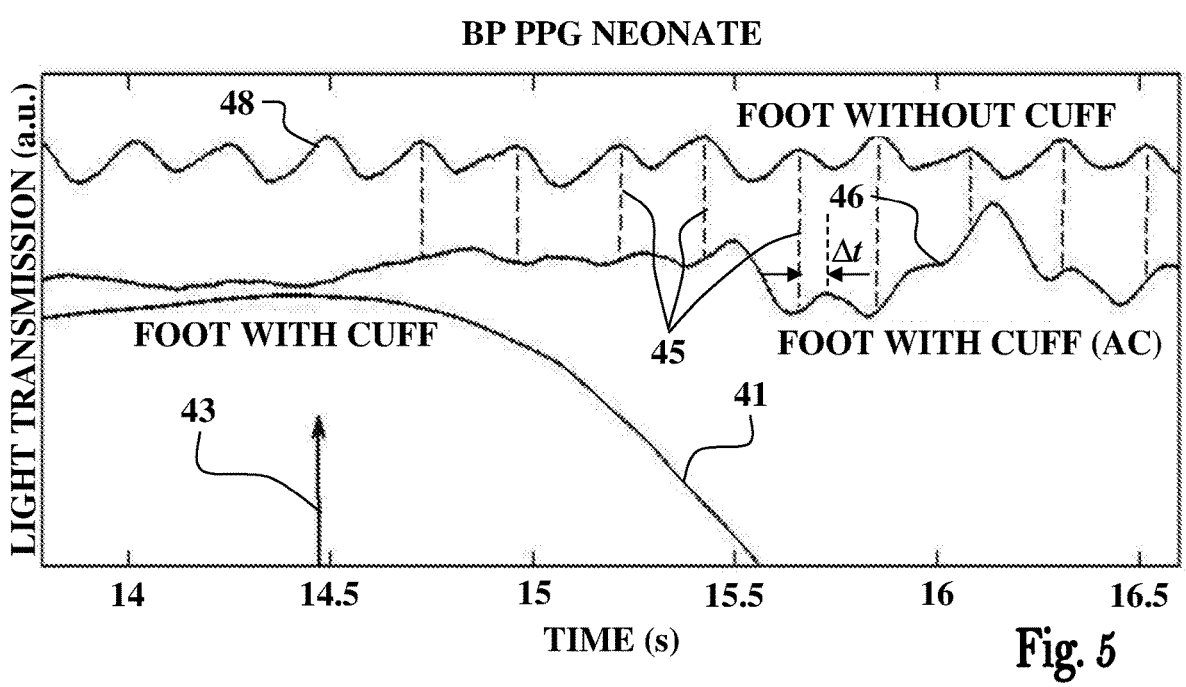
FIG. 5 shows raw light transmission and AC PPG signal curves taken from a foot of a neonate during the deflation of a cuff situated over the ankle and a cuff-free PPG signal simultaneously taken from the other foot of the neonate.

The controller 62 may be further configured to determine the presence and the lengths of the time delays Δt (see FIGS. 4 and 5) between the PPG pulses measured in the pressure-affected body part by the PPG probe of the measuring unit 70 and the PPG pulses measured in the pressure/cuff-free body part by the reference PPG probe of the reference measuring unit 70r. The determined time delays Δt may be used by the controller 62 to improve the process of differentiating between changes associated with the reappearance of the PPG pulses and the changes which are due to interfering noise.

In some embodiments the controller 62 may comprise an input to receive signals from sound transducer 76k (e.g., piezoelectric transducer) that is located under the cuff 88 and configured and operable to detect the Korotkoff sounds in the pressure-affected body part, and produce responsive acoustic data. The controller 62 may be configured and operable to process the acoustic (Korotkoff sounds) data together with the optical data from the cuff-free limb and pressure data responsively received, and determine the average systolic/diastolic (or mean) blood pressure of the examined subject using one or more of the methods described hereinabove or hereinbelow.

Figure 10:
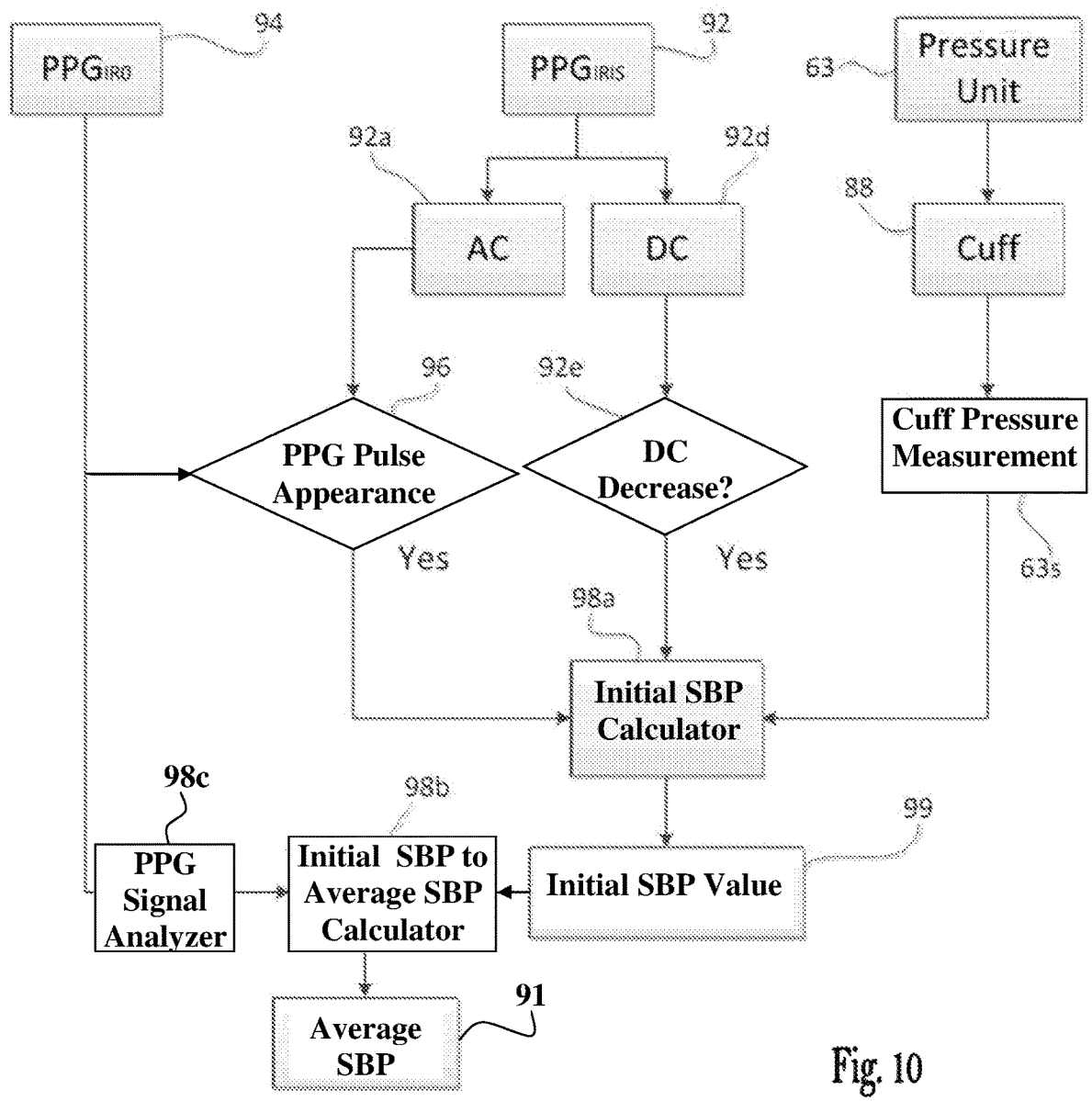
FIG. 10 is a flowchart demonstrating a PPG-based blood pressure measurement process according to some possible embodiments.

The PPG probe of the reference measuring unit 70r is used to measure pressure-free reference PPG signals 76r from a pressure-free body part (e.g., in a contralateral limb) of the examined subject, which are used for computing the correction factor as described hereinabove. With reference to FIG. 10, the optical data (76r) obtained by the reference PPG probe of the measuring unit (70r) may be used to generate a reference pressure free $PPG_{IRO}$ curve 94. In this example the pulse identifying unit 96 is configured to receive the PPG pulses of the reference pressure-free $PPG_{IRO}$ curve 94 and use them as a guiding reference to differentiate between changes identified in the pulsatile components which are due to the reappearance of the PPG pulses and the changes which are due to interfering noise induced in the pulsatile components. In this way the accuracy of the initial SBP value 99 determined by the decision unit 98a is further improved.

The pulse identifying unit 96 may be further configured to determine the presence and the lengths of the time delays Δt (see FIGS. 4 and 5) between the PPG pulses identified in the pulsatile components 92a from the PPG signals measured in the pressure-affected body part and the PPG pulses in the reference pressure free $PPG_{IR0}$ curve 94 (i.e., in the pressure/cuff-free body part). Detection of the presence and the lengths of the time delays Δt may be used in some embodiments to improve the accuracy of the differentiating functionality (between changes associated with the reappearance of the PPG pulses and the changes which are due to interfering noise) of the pulse identifying unit 96. For example, in some embodiments the presence of time delays Δt of suitable lengths (e.g., in the range of 100-200 millisecond) indicates the appearance of PPG pulses in the tissue (distal to the cuff) in the pressure-affected body part.

The pulse identifying unit 96 is further configured and operable to receive and process the AC component 92a of the PPG signal measured in the pressure-affected body part, identify in it reappearance of PPG pulses, in case descending pressure conditions are being applied (or vanishing of the PPG pulses, if ascending pressure conditions are being applied), and issue an indication upon identifying the blood-pressure-pulse related event. The trend monitoring unit 92e is configured and operable to receive and process the DC component 92d of the PPG signal measured in the pressure-affected body part, identify in it a change in the trend of the DC curve 92d, and issue an indication upon identifying the blood-pressure pulse related event.

The initial SBP calculator unit 98a receives and processes the instantaneous absolute pressure data from the cuff pressure measurement unit 63s. In some embodiments, the Initial SBP Calculator unit 98a is configured to receive and process the blood-pressure-pulse related events issued by the pulse monitoring unit 96 and from the trend monitoring unit 92e, and based on the identified blood-pressure-pulse related events determine the initial blood pressure value 99. For example, and without being limiting, the Initial SBP Calculator unit 98a may be configured and operable to determine the initial blood pressure value based on the highest air pressure in which one of the blood-pressure pulse related event was detected (i.e., based on indication from the pulse monitoring unit 96 if pulse reappear/vanish is identified in the AC component 92a at a higher pressure than that at which a trend change is identified in the DC component 92d, and wise versa).

In some embodiments the initial SBP calculator unit 98a is configured and operable to determine the initial SBP value 99 of the subject based on the first blood-pressure pulse related event identified from the DC component 92d by the trend identifying unit 92e, from the AC component 92a by the pulse identifying unit 96, or from the absolute pressure data received from the pressure measurement unit 63s.

In preferred embodiments the PPG reference signal (curve 94) from the reference measurement unit (70r) is used to create pressure-free PPG pulse signals (76r) that provide information on the variability of one or more PPG signal parameters, such as $I_D$ (pulse maximum), $I_S$ (pulse minimum) or $I_D$-$I_S$ (amplitude) of the measured pulse signal. The PPG analyzer unit 98c is configured to receive and process the PPG reference signal and compute the average of one of the PPG signal parameters in some of the PPG pulse reference signals (i.e., in the time window 55). The processing unit 98c then calculates a correction factor for determining the average SBP value 91 of the examined subject, as described hereinabove in the initial SBP to Average SBP Calculator unit 98b.

In some embodiments the PPG signal from the reference measurement unit (70r) is used to provide PPG reference pulse signals that provide information on the variability of one or more PPG signal parameters, such as $I_D$, $I_S$ or $I_D$-$I_S$. In some embodiments the processing unit 98c is configured to determine the average of the PPG pulse parameters of some of the measured PPG reference signal and use it to calculate a correction factor for determining the average of SBP value of the examined subject, using an initial SBP value determined based on measured Korotkoff sounds or by oscillometry techniques.

In some embodiments the pressure device is configured and operable to apply ascending pressure conditions over the examined organ, and generate pressure data indicative of the pressure applied over said organ. The control unit may be accordingly configured and operable to detect in the pulsatile AC component (92a), in the baseline DC component (92d), and/or in the measured Korotkoff sounds, the blood-pressure pulse related event as the vanishing of the blood-pressure pulse once the pressure applied over the examined organ becomes greater than the systolic blood pressure. The control unit is further configured to identify an initial blood pressure value of the subject from the pressure data based on at least one of the blood-pressure pulse related events identified in the PPG pulsatile component, PPG baseline component, and/or measured Korotkoff sounds, and determine accordingly the initial blood pressure value of the subject. For example, in case descending pressure conditions are being applied, the control unit may be configured and operable to determine the SBP as the maximal identified air pressure at which the blood-pressure-pulse related events were detected in the pulsatile AC component, the baseline DC component, and/or the measured Korotkoff sounds (or as the minimal pressure applied when these blood-pressure related events occurred, if ascending pressure conditions are being applied).

The PPG-based measurement techniques of the present application are of particular importance for SBP measurement in the following scenarios:

In populations who cannot always demonstrate Korotkoff sounds such as infants, and in particular neonates. In neonates blood pressure measurement is generally done through oscillometry, which is not accurate, and the PPG-based technique can replace it.

The problem of weak or absent Korotkoff sounds also appears in patients of very low blood pressure as often occurs in cardiac intensive care units.

In noisy environment such as ambulance or helicopter, where Korotkoff sounds cannot be properly heard.

In the lower limbs in which Korotkoff sounds are generally absent. The ankle/brachial pressure ratio is clinically important for the assessment of stenosis in the lower limbs.

As an automatic accurate method for SBP measurement. The available commercial devices for automatic blood pressure measurement are based on oscillometry, which is not accurate and in general are not based on Korotkoff-sounds-based sphygmomanometry, because of artifacts. The automatic PPG-based techniques of the present application can provide accurate assessment of SBP.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A system for determining an average of an arterial blood pressure parameter of an examined subject, wherein said system is configured to determine said arterial blood pressure parameter by adapting an initial instantaneous single-pulse blood pressure parameter value of the examined subject to spontaneous blood pressure fluctuations over a time window, the system comprising:
 a pressure device configured and operable to apply changing pressure conditions over a body part of the examined subject, and generate pressure measurement data indicative of a pressure-applied over said body part by said pressure device;
 a first measuring unit configured and operable to measure blood-pressure-pulse related signals in a body part affected by said changing pressure conditions, and generate blood-pressure-pulse related measurement data indicative thereof;
 a second measuring unit configured and operable to measure blood-pressure-pulse related signals in a pressure-free body part of the examined subject, said pressure-free body part is not directly affected by said changing pressure conditions, and generate reference blood-pressure-pulse related measurement data indicative thereof;
 a control unit configured and operable to operate said pressure device to apply said changing pressure conditions and simultaneously operate said first and second measuring units, the control unit comprising:
 an event detector configured and operable to process and analyze the blood-pressure-pulse related measurement data generated by the first measuring unit and identify a blood-pressure-pulse related event therein associated with the applied changing pressure conditions, and process and analyze the pressure measurement data generated by the pressure device and determine based on the identified blood-pressure-pulse related event an initial instantaneous single-pulse blood pressure parameter value of the examined subject;
 a signal selector configured and operable to identify in the reference blood-pressure-pulse related measurement data a center blood-pressure-related pulse simultaneous with the identified blood-pressure-pulse related event and define in said reference blood-pressure-pulse related measurement data a time window having a predetermined number of consecutive blood-pressure-related pulses centered about the identified center blood-pressure-related pulse, said consecutive blood-pressure-related pulses reflect the spontaneous blood pressure fluctuations of said examined subject;
 a factor generator configured and operable to determine a respective characteristic parameter for each of the predetermined number of consecutive blood-pressure-pulses within the defined time window, and calculate a correction factor from an average of said respective predetermined number of characteristic parameters; and
 a blood pressure evaluator configured and operable to determine the average arterial blood pressure parameter of the examined subject by adapting said initial instantaneous single-pulse blood pressure parameter value in accordance with said correction factor, thereby adapting said initial instantaneous single-pulse blood pressure parameter in accordance with said spontaneous blood pressure fluctuations of the examined subject.

2. The system of claim 1 wherein the pressure device is an air pressure cuff configured to apply the changing pressure conditions over-a the first body part of the examined subject, and wherein the changing pressure conditions are either monotonic descending or ascending changing air pressure.

3. The system of claim 2 wherein the first measuring unit comprises at least one of the following: a photoplethysmographic (PPG) sensor configured and operable to measure PPG pulses in the body part affected by the changing pressure conditions and generate PPG measurement data indicative thereof; an optical probe configured and operable to measure light transmission changes associated with blood-pressure-pulses in the body part affected by the changing pressure conditions and generate optical measurement data indicative thereof; an acoustic sensor configured and operable to measure Korotkoff sounds in the body part affected by the changing pressure conditions and generate acoustic measurement data indicative thereof; and an air pressure sensor configured and operable to measure oscillatory air pressure changes in the pressure cuff associated with arterial blood pressure in the body part affected by the changing pressure conditions and generate -air pressure measurement data indicative thereof.

4. The system of claim 3 wherein the changing pressure conditions applied by the pressure device are monotonically descending starting from a pressure level greater than a systolic blood pressure of the examined subject, and wherein the control unit is configured and operable to identify the blood-pressure-pulse related event in the blood-pressure-pulse related data obtained from the first measuring unit as either appearance of a blood-pressure-pulse related signal in either the optical, acoustic, PPG, or air pressure measurement data, or as a change in a trend of a baseline component of either the optical measurement data or the PPG measurement data.

5. The system of claim 4 wherein the arterial blood pressure parameter is MBP, and wherein the control unit is configured and operable to identify the blood-pressure-pulse related event as an air pressure pulse of maximal amplitude identified in the air pressure measurement data.

6. The system of claim 1 wherein the arterial blood pressure parameter comprises systolic blood pressure (SBP), diastolic blood pressure (DBP) and/or mean blood pressure (MBP).

7. The system of claim 1 wherein the second measuring unit comprises at least one of the following: a PPG sensor configured and operable to measure PPG signals in the pressure-free body part and generate reference PPG measurement data indicative thereof; an optical probe configured and operable to measure light transmission changes associated with blood-pressure-pulses in the pressure-free body part and generate reference optical measurement data indicative thereof; and a pressure sensor configured and operable to measure oscillatory pressure changes associated with oscillatory arterial blood pressure changes in the pressure-free body part, and generate reference oscillatory measurement pressure data indicative thereof.

8. The system of claim 1 wherein the factor generator is configured and operable to compute the correction factor as a ratio of an average value of the respective characteristic parameter over the predetermined number of consecutive blood-pressure-pulses within the defined time window, and a value of the characteristic parameter determined for the identified center blood-pressure-related pulse.

9. The system of claim 8 wherein the characteristic parameter is based on at least one of the following: pulse maximum, pulse minimum, pulse amplitude, a ratio of pulse amplitude and pulse minimum, a ratio of pulse amplitude and pulse maximum, ratio of pulse maximum and pulse minimum.

10. The system of claim 8 wherein the signal selector is configured and operable to identify the center blood-pressure-related pulse in the reference blood-pressure-pulse related measurement data as a blood-pressure-pulse occurring in the pressure-free body part at a point in time at which the blood-pressure-pulse related event occurred in the body part affected by the changing pressure conditions.

11. The system of claim 10 wherein the predetermined number of blood-pressure-pulses is in the range of 5 to 31, inclusive.

12. A method of determining an average of at least one blood pressure parameter of an examined subject, the method comprising applying changing pressure conditions over a body part of the examined subject and simultaneously performing the following steps:
measuring the pressure applied over said body part affected by said changing pressure conditions;
measuring blood-pressure-pulse related signals in the body part affected by said changing pressure conditions and generating blood-pressure-pulse related data indicative thereof;
measuring blood-pressure-pulse related signals in a pressure-free body part of the examined subject and generating reference blood-pressure-pulse related measurement data indicative thereof, said pressure-free body part is not directly affected by said changing pressure conditions;
identifying in the blood-pressure-pulse related data a blood-pressure-pulse related event associated with the pressure applied over the body part affected by said changing pressure conditions;
determining an initial instantaneous single-pulse blood pressure parameter value of the examined subject based on the pressure applied on the body part affected by said changing pressure conditions as measured when said blood-pressure-pulse related event occurred;
identifying in the reference blood-pressure-pulse related measurement data a center blood-pressure-related pulse associated with the blood-pressure-pulse related event;
defining in said reference blood-pressure-pulse related measurement data a window having a predetermined number of consecutive blood-pressure-related pulses centered about the identified center blood-pressure-related pulse, said consecutive blood-pressure-related pulses reflect the spontaneous blood pressure fluctuations of said examined subject;
determining a respective characteristic parameter for each of the consecutive blood-pressure-related pulses within the defined window;
calculating a correction factor from an average of said respective predetermined number of characteristic parameters; and
determining the average of the at least one blood-pressure parameter by adapting said initial instantaneous single-pulse blood pressure parameter value in accordance with said correction factor, thereby adapting said initial instantaneous single-pulse blood pressure parameter in accordance with said spontaneous blood pressure fluctuations of the examined subject.

13. The method of claim 12 comprising applying a pressure higher than a systolic blood pressure (SBP) value of the examined subject over the body part affected by the changing pressure conditions, and thereafter applying decreasing pressure conditions thereover, said pressure higher than the SBP value of the examined subject is applied for a predefined period of time sufficient to induce increased blood flow in the body part affected by the changing pressure conditions after the pressure is reduced below the SBP value.

14. The method of claim 12 wherein the changing pressure conditions are monotonically descending starting from a pressure level greater than a systolic blood pressure of the examined subject, and wherein the blood-pressure-pulse related event is an indication that the pressure applied over the body part affected by the changing pressure conditions became smaller than the systolic blood pressure of the examined subject.

15. The method of claim 12 wherein the changing pressure conditions are monotonically ascending until reaching a pressure level greater than a systolic blood pressure of the examined subject, and wherein the blood-pressure-pulse related event is an indication that the pressure applied over the body part affected by the changing pressure conditions became greater than the systolic blood pressure of the examined subject.

16. The method of claim 12 comprising determining the correction factor by computing a ratio of an average value of the respective characteristic parameter over the predetermined number of consecutive of blood-pressure-pulses within the defined time window and a characteristic parameter corresponding to the center blood-pressure-related pulse.

17. The method of claim 12 further comprising assessing sympathetic nervous activity of the examined subject by deriving a parameter associated with the variability of the blood-pressure-pulse related signals measured in the pressure-free body part not directly affected by said changing pressure conditions.

18. The method of claim 12, where the two blood pressure parameters of an examined subject are the systolic blood pressure and diastolic blood pressure, and the average pulse pressure of the examined subject is calculated from the difference between the average systolic blood pressure and the average diastolic blood pressure.

19. A method of determining a corrected value of pulse pressure of an examined subject, the method comprising affecting changing pressure conditions over a body part of the examined subject and simultaneously performing the following steps:
measuring a pressure applied over said body part affected by said changing pressure conditions;
measuring blood-pressure-pulse related signals in the body part affected by said changing pressure conditions and generating blood-pressure-pulse related data indicative thereof;
measuring blood-pressure-pulse related signals in a pressure-free body part of the examined subject and generating reference data indicative thereof, said pressure-free body part is not directly affected by said changing pressure conditions;
identifying in the blood-pressure-pulse related data a systolic blood-pressure-pulse related event and a diastolic blood-pressure-pulse related event associated with the pressure applied over the body part affected by said changing pressure conditions;
determining an instantaneous single-pulse systolic blood pressure value of the examined subject based on the pressure applied on the body part affected by said changing pressure conditions as measured when the blood-pressure-pulse related event associated with systolic blood pressure occurred;

determining an initial instantaneous single-pulse diastolic blood pressure value of the examined subject based on the pressure applied on the body part affected by said changing pressure conditions as measured when the blood-pressure-pulse related event associated with diastolic blood pressure occurred;

identifying in the reference blood-pressure-related pulse measurement data blood-pressure-related pulses associated with the systolic and diastolic blood-pressure-pulse related events;

determining a first amplitude value for the reference blood-pressure-related pulse simultaneous with the systolic blood-pressure-pulse related event;

determining a second amplitude value for the reference blood-pressure-related pulse simultaneous with the diastolic blood-pressure-pulse related event;

calculating a diastolic correction factor defined as the ratio of the second amplitude value to the first amplitude value;

calculating a corrected diastolic blood pressure by multiplying the initial instantaneous diastolic blood pressure value with the diastolic correction factor; and determining corrected pulse pressure by subtracting the corrected diastolic blood pressure from the instantaneous single-pulse systolic blood pressure value.

20. The method of claim 19, where the systolic blood-pressure-pulse related event is the reappearance of the PPG signal or the Korotkoff sounds when the changing pressure conditions decreases below SBP value, and wherein the diastolic blood-pressure-pulse related event is the disappearance of the Korotkoff sounds when the changing pressure conditions decreases below DBP value.

* * * * *